(12) United States Patent
Guldberg

(10) Patent No.: US 8,105,782 B2
(45) Date of Patent: Jan. 31, 2012

(54) MATERIALS AND METHODS RELATING TO NUCLEIC ACID AMPLIFICATION AND PROFILING

(75) Inventor: Per Guldberg, Copenhagen (DK)

(73) Assignee: Cancer Research Technology Limited, London (GB)

( * ) Notice: Subject to any disclaimer, the term of this patent is extended or adjusted under 35 U.S.C. 154(b) by 1753 days.

(21) Appl. No.: 10/399,899

(22) PCT Filed: Oct. 23, 2001

(86) PCT No.: PCT/GB01/04707
§ 371 (c)(1),
(2), (4) Date: Oct. 3, 2003

(87) PCT Pub. No.: WO02/34942
PCT Pub. Date: May 2, 2002

(65) Prior Publication Data
US 2004/0048275 A1    Mar. 11, 2004

(30) Foreign Application Priority Data

Oct. 23, 2000 (GB) .................................. 0025913.5
Mar. 26, 2001 (GB) .................................. 0107547.2

(51) Int. Cl.
  *C12Q 1/68* (2006.01)
  *C12P 19/34* (2006.01)
  *C07H 21/04* (2006.01)
(52) U.S. Cl. .................... 435/6.12; 435/91.2; 536/24.33
(58) Field of Classification Search ............. 435/6, 91.2; 536/24.33, 24.31, 24.32
See application file for complete search history.

(56) References Cited

U.S. PATENT DOCUMENTS

| | | | | |
|---|---|---|---|---|
| 5,871,908 | A | * | 2/1999 | Henco et al. ............. 435/6 |
| 6,174,670 | B1 | | 1/2001 | Wittwer et al. |
| 6,335,165 | B1 | * | 1/2002 | Navot et al. ............... 435/6 |
| 6,346,386 | B1 | * | 2/2002 | Elenitoba-Johnson ..... 435/6 |
| 6,410,273 | B1 | * | 6/2002 | Crouzet et al. ........... 435/91.1 |
| 6,858,388 | B2 | * | 2/2005 | Markowitz et al. ........ 435/6 |

FOREIGN PATENT DOCUMENTS

| | | |
|---|---|---|
| DE | 198 25 314 A1 | 3/2000 |
| DE | 198 53 398 C1 | 3/2000 |
| EP | 1 195 443 A2 | 4/2002 |
| WO | WO 96/39535 | 12/1996 |
| WO | WO 97/46705 | 12/1997 |
| WO | WO 97/46714 | 12/1997 |
| WO | WO 99/55905 | 11/1999 |
| WO | WO 00/70090 | 11/2000 |

OTHER PUBLICATIONS

Eads et al. MethyLight: a high-throughput assay to measure DNA methylation. Nucleic Acids Res., vol. 28, pp. e32 (i)-e32 (viii), 2000.*
Aggerholm et al. Extensive Intra-and Interindividual heterogeneity of p15INK4B methylation in acute myeloid leukemia. Cancer Res., vol. 59, pp. 436-441, 1999.*
Aggerholm, A., et al., "Extensive intra- and interindividual heterogeneity of p15$^{INK4B}$ methylation in actue myeloid leukemia", Cancer Research, 59, pp. 436-441 (1999).
Eads, C. A., et al., "MethyLight: a high-throughput assay to measure DNA methylation", Nucleic Acids Research, 28, E32 (2000).
Frommer, M., et al., "A genomic sequencing protocol that yields a positive display of 5-methylcytosine residues in individual DNA strands", Proc. Natl. Acad. Sci., 89, pp. 1827-1831 (1992).
Guldberg, P., et al., "Detection of mutations in GC-rich DNA by bisulphate denaturing gradient gel electrophoresis", Nucleic Acids Research, 26, pp. 1548-1549 (1998).
Herman, J. G., et al., Methylation-specitic PCR: a novel PCR assay for methylation status of CpG Islands. Proc. Natl. Acad. Sci., 93, pp. 9821-9826 (1996).
Ririe, K. M., et al., "Product differentiation by analysis of DNA melting curves during the polymerase chain reaction", Anal. Biochem., 245, pp. 154-160 (1997).
Worm, J., et al., "In-tube DNA methylation profiling by fluorescence melting curve analysis", Clin. Chem., 47, pp. 1183-1189 (2001).
Lipsky, R., H., et al., "DNA melting analysis for detection of single nucleotide polymorphisms", Clin. Chem. 47, pp. 635-644 (2001).
Schaeffer, R., et al., "Point mutations change the thermal denaturation profile of a short DNA fragment containing the lactose control elements, Comparison between experiment and theory." EMBO J. 1, pp. 99-105 (1982).
Translation of JP Office Action for JP Application No. 2002-537911.
Deepak De Silva et al., "Monitoring hybridization during polymerase chain reaction", Journal of Chromatography B, 741: 3-13 (2000).
Ying Wu et al., "Improvement of fragment and primer selection for mutation detection by denaturing gradient gel electrophoresis", Nucleic Acids Research, 26 (23): 5432-5440 (1998).
Soren Germer et al., "Single-Tube Genotypeing without Oligonucleotide Probes", Genome Research, 1999, pp. 72-78.
Michael Zeschnigk et al., "Imprinted segments in the human genome: different DNA methylation patterns in the Prader-Willi/Angelman syndrome region as determined by the genomic sequencing method", Human Molecular Genetics, 1997, vol. 6, No. 3, pp. 387-395.
Per Guldberg et al., "Profiling DNA methylation by melting analysis", Methods, 27, (2002), pp. 121-127.

* cited by examiner

*Primary Examiner* — Prabha Chunduru
(74) *Attorney, Agent, or Firm* — Stephen A. Bent; Folely & Lardner LLP

(57) ABSTRACT

The invention provides improved methods for determining the methylation profile of a nucleic acid sequence and for determining one or more base changes in the target nucleic acid sequence as compared to a corresponding control sequence. The methods are one-step methods which can be incorporated with known amplification techniques such as PCR. The invention also provides methods for determining changes in nucleic acid sequences either via their methylation profile or owing to mutations of one or more bases.

13 Claims, 12 Drawing Sheets

MATERIALS AND METHODS RELATING TO NUCLEIC ACID AMPLIFICATION AND PROFILING

FIELD OF THE INVENTION

The present invention concerns materials and methods relating to improved nucleic acid amplification and profiling. Particularly, but not exclusively, the present invention concerns the in-tube DNA methylation profiling by, for example, fluorescence melting curve analysis.

BACKGROUND OF THE INVENTION 5-methylcytosine ($m^5C$) occurs in the context of CpG dinucleotides and is the most abundant covalently modified base in the genomes of vertebrates. Areas of high CpG dinucleotide density, so called 'CpG islands', are spread throughout the genomes and usually map to gene promoter regions. Methylation of promoter CpG islands is associated with histone deacetylation and transcriptional silencing (1), and is essential for normal embryonic development, genomic imprinting and X-chromosome inactivation. Recently, somatic de novo methylation of CpG islands in tumor suppressor genes has been implicated in tumorigenesis, and aberrant methylation of imprinted genes is associated with several inherited human diseases (1-3). The central role of DNA methylation in normal and disease-related processes has resulted in a variety of methods to detect and characterise normal and aberrant methylation patterns in biological and clinical specimens.

In standard PCR and cloning procedures, information about $m^5C$ and other covalent base modifications in genomic DNA is lost. Therefore, current PCR methods for detecting and mapping $m^5C$ in specific genes rely on treatment of genomic DNA with methylation-sensitive restriction endonucleases or sodium bisulfite prior to amplification. Bisulfite converts unmethylated cytosines to uracil, while methylated cytosines remain unreactive (4). A specific target sequence can subsequently be amplified with primers specific for bisulfite-converted DNA and examined for its $m^5C$ content. The golden standard among bisulfite methods is genomic sequencing that provides a positive display of $m^5C$ at specific CpG sites in virtually any stretch of DNA (5). More simple methods using bisulfite-converted DNA as template include methylation-specific PCR (MSP) (6), methylation-sensitive single nucleotide primer extension (7) and procedures based on the use of restriction endonucleases (8;9).

Despite the obvious advantages of the above methods, they all entail a two-step procedure, comprising initial PCR amplification and subsequent product analysis, usually by gel electrophoresis. Furthermore, with the exception of genomic sequencing, they are limited to the analysis of one or a few CpG sites in each setting.

SUMMARY OF THE INVENTION

The present inventors herein describe a new in-tube PCR assay for detection of aberrant DNA methylation, which uses a thermal cycler integrated with a signal detector, e.g. a fluorimeter (light cycler) (10) and exploits differences in melting temperature ($T_m$) between methylated and unmethylated alleles following bisulfite treatment.

Thus, the present invention provides a method of determining a methylation profile for a target nucleic acid sequence said method comprising (a) treating a nucleic acid sequence with a bisulfite, preferably sodium bisulfite, to convert unmethylated cytosines within the nucleic acid sequence to uracil thereby creating a converted nucleic acid sequence;

(b) amplifying said treated nucleic acid sequence using oligonucleotide primers specific only for said converted nucleic acid sequence, said amplification conditions including the incorporation of a signal agent in the amplified nucleic acid, said signal agent being capable of providing a distinction between double-stranded and single-stranded nucleic-acid;

(c) detecting the amount of said signal agent during conversion (transition) of the nucleic acid between double-stranded and single-stranded as a result of a temperature change;

(d) determining the methylation profile of said target nucleic acid sequence by measuring the amount of signal agent detected during said temperature change.

In a preferred embodiment of the present invention, the transition of the nucleic acid will be from double-stranded to single-stranded as a result of a temperature increase. Alternatively, the change in signal could be detected during the transition from single-stranded to double-stranded as a result of a temperature decrease.

The target nucleic acid sequence may be any nucleic acid sequence derived from animal, plant or prokaryotic organism. Preferably, the target nucleic acid sequence is derived from a human.

Most conveniently, the signal agent is a dye, e.g. a fluorescent dye that can be detected using a light meter. The preferred method of detection is the use of a fluorimeter (10). DNA melting curves are acquired by measuring the fluorescence of a double-stranded DNA binding fluorescent dye e.g. SYBR Green I, during a temperature transition. The temperature transition is may be linear or as near to linear as is reasonable possible.

Although SYBR Green I is the preferred fluorophore in the present invention, the skilled person will appreciate that other fluorophores may equally be used. Examples of such fluorophores include acridine orange, propidium iodide, ethidium bromide, mithramycin, chromomycin, olivomycin, Hoechst H33258, Hoechst H33342, DAPI (4',6-diamidino-2-phenylindole), TOPRO, TOTO, YOPRO, YOYO and Picogreen.

Alternatively, the detection of the signal agent can be achieved using UV or energy transfer mechanisms where the appropriate signal agent is used. The signal agent may in fact comprise two dyes used in combination. For example, it is possible to dye-label nucleotides where the dye is covalently linked to the DNA. A two dye system may be created which allows distinction between single stranded and double stranded nucleic acid.

As mentioned above, the present invention may be performed using a thermal cycler having a signal detector. However, it is also possible to carry out the method using a standard PCR machine in combination with a further machine that allows the sample to be heated and a signal to be detected. An example of such a further machine is a Dash-system (ThermoHybaid). This further machine may be supplied as part of a kit for carrying out the invention (see below).

The determination of the methylation profile may be gained by comparison with a control. For example, if the target nucleic acid under test is derived from a tumour e.g. melanoma, then a control may conveniently be a nucleic acid sequence from a normal melanocyte.

In a second aspect of the present invention, the inventors have provided a method that allows the integration of melting curve analysis described above with PCR for in-tube detection of single-base mutations.

Theoretical and experimental studies have shown that DNA melts in a series of steps where each step represents the melting of a discrete segment, called a 'melting domain'.

A base substitution or other type of mutation may change the $T_m$ of the domain in which it resides with up to 0.5° C. Mutation resolution based on differences in melting properties may be accomplished by denaturing gradient gel electrophoresis (DGGE), where an increasing gradient of denaturants simulates a temperature gradient within the gel (Abrams and Stanton, 1992). Using an instrument for very accurate stepwise temperature incrementation, Schaeffer et al (1983) showed that DNA fragments differing by a single base substitution showed different $T_m$s, as determined by UV absorbance measurements. Recently, instruments have become available that have integrated a microvolume fluorimeter with a rapid temperature cycler. Using these instruments, melting curves may be acquired immediately after PCR by measuring the fluorescence of a double stranded DNA dye during a linear temperature transition. This has been used to differentiate between unrelated PCR products with no sequence homology (Ririe et al, 1997). However, detection of small mutations by using these microvolume fluorimeter-based thermal cyclers is severely hampered for several reasons:

1) For some mutations, the net $T_m$ is unchanged despite the presence, in solution, of homo- and heteroduplices.
2) Concentrations of salt and dyes may have a significant impact on the width and absolute position of a PCR product's melting peak.
3) The rapid temperature transition and the relatively poor temperature control may affect the absolute $T_m$ and cause significant tube-to-tube variation.

Hence, detection of small changes in $T_m$ due to single-base changes may only be accomplished by adding an appropriate internal control.

The principle of this second aspect of the invention is that the internal control for $T_m$ is contained within the PCR product itself. FIG. 5A shows the melt map of exon 2 of the N-ras proto-oncogene. FIG. 5B shows the melt map of the same region after the artificial addition of a low-temperature control melting domain ('a') and a high-temperature melting domain ('GC-clamp') ('c'). The artificial domains are easily incorporated via the PCR primers. The GC-clamp introduces a new highest-melting domain and works as a "handle" to keep the strands together. The control domain has a $T_m$ that is 2-3° C. lower than the $T_m$ of the domain containing the sequence of interest. The height and width of the melting peak of the control domain, the area under the melting peak, and the $T_m$ of the melting peak are used as control parameters. Thus, the second aspect of the present invention provides a method of detecting one or more base mutations in a target nucleic acid sequence comprising the steps of (a) integrating into the nucleic acid sequence a low-temperature control melting domain and a high-temperature melting domain (GC-clamp);
(b) amplifying the nucleic acid sequence having the integrated low-temperature control melting domain and the GC-clamp using oligonucleotide primers;
(c) providing the amplified stranded nucleic acid with a signal agent that distinguishes between double-stranded nucleic acid sequences and single-stranded nucleic acid sequences;
(d) detecting the change in signal of said signal agent during transition of the nucleic acid from double-stranded to single-stranded as a result of a temperature increase; and
(e) determining the presence of one or more base mutations in the target nucleic acid sequence by comparing its melting peak with that of a control nucleic acid sequence tested under comparable conditions.

It is preferable that the low-temperature control melting domain and the GC-clamp are incorporated as part of the PCR amplification step. Preferably, PCR primers are provided that contain these sequences and thus, the resulting PCR double stranded amplification product will comprise the two domains as well as the target nucleic acid sequence (intermediate-melting domain).

In order to determine whether the target nucleic acid sequence contains one or more mutations (differences) compared to a control nucleic acid sequence, the method of the second aspect of the invention is carried out on both sequences (target and control) in comparable, preferably identical, conditions. For example, the target nucleic acid sequence may be from a tumour cell, e.g. a melanoma cell, and the control may be from a corresponding normal cell, e.g. a melanocyte. In this example, the determination made in accordance with step (e) of the method will be the comparison of the intermediate melting domain and the low-melting domain of the target nucleic sequence with the intermediate melting domain and the low-melting domain of the control nucleic sequence. See detailed description for illustrated examples.

As mentioned above the signal agent may be a signal that specifically binds to double-stranded nucleic acid and not single-stranded nucleic acid. Thus, as the nucleic acid sequence is heated and the strands become denatured, the signal will start to disappear and the change can be measured. Alternatively, multiple signals may be used where a change in signal type identifies the distinction between double-stranded and signal-stranded nucleic acid sequence.

All aspects of the present invention may be used to aid in the diagnosis of a disease state associated with methylation profiles of nucleic acid. For example, with regard to mammalian cells, development and cell differentiation abnormalities are often associated with nucleic acid methylation levels. Thus, the present invention provides a quick and efficient way in which these levels or differences in levels can be determined and monitored. Likewise, in plant breeding it is often important to known changes in methylation levels of plant DNA. Further, the invention may be used to provide a database of nucleic acid methylation profiles for use in disease diagnosis. These databases or the methods of the invention may be used to aid a medical practitioner in a method of medical treatment.

In a further aspect of the present invention, there is provided a research tool or kit for carrying out the methods of the invention described above. The tool or kit may comprise several nucleic acid primers designed to determine different pathologies. The kit may take the form of a chip or bead comprising a solid support onto which are fixed a plurality of primers for determining the methylation profiles or a population of nucleic acid sequences. The kit will preferably also comprise the components required to carry out the PCR reaction as well as detection compounds such as fluorophores (see above). The kit may also comprise written instruction for carrying out the method according to the first or second aspect of the present invention.

Thus, the invention has many applications in the field of medical research diagnosis and treatment. The methods of the invention may be used as research tools for testing new and known genes for aberrant DNA methylation or mutation patterns. The methods may be used as screening assays to identify novel correlation between known/novel genes and genetic disorders or pathologies.

One of the most important uses of the invention will be in the field of diagnosis. For example, the methods may be used to identify a particular methylation pattern associated with different cancer types, genetic disorders, metabolic diseases or other pathologies including age related pathologies. The results from such a method would aid a medical practitioner in determining the type of treatment required by the patient. Further, the method may be used to identify a particular methylation pattern that can predict the responsiveness of tumours to chemotherapy (see for example, Manel Estellel, et al, New England J. Medicine, vol. 343, No. 19, 2000).

BRIEF DESCRIPTION OF THE DRAWINGS

Aspects of the present invention will now be further described by way of example with reference to the accompanying drawings, by way of example and not limitation. Further aspects of the invention will be apparent to those of ordinary skill in the art. All documents referred to herein are incorporated by reference.

In the Figures:

FIG. 5A shows the melt map of exon 2 of the N-ras proto-oncogene. FIG. 5B shows the melt map of the same region after the artificial addition of a low-temperature control melting domain ('a') and a high-temperature melting domain ('GC-clamp') ('c').

DETAILED DESCRIPTION

Figure 1:
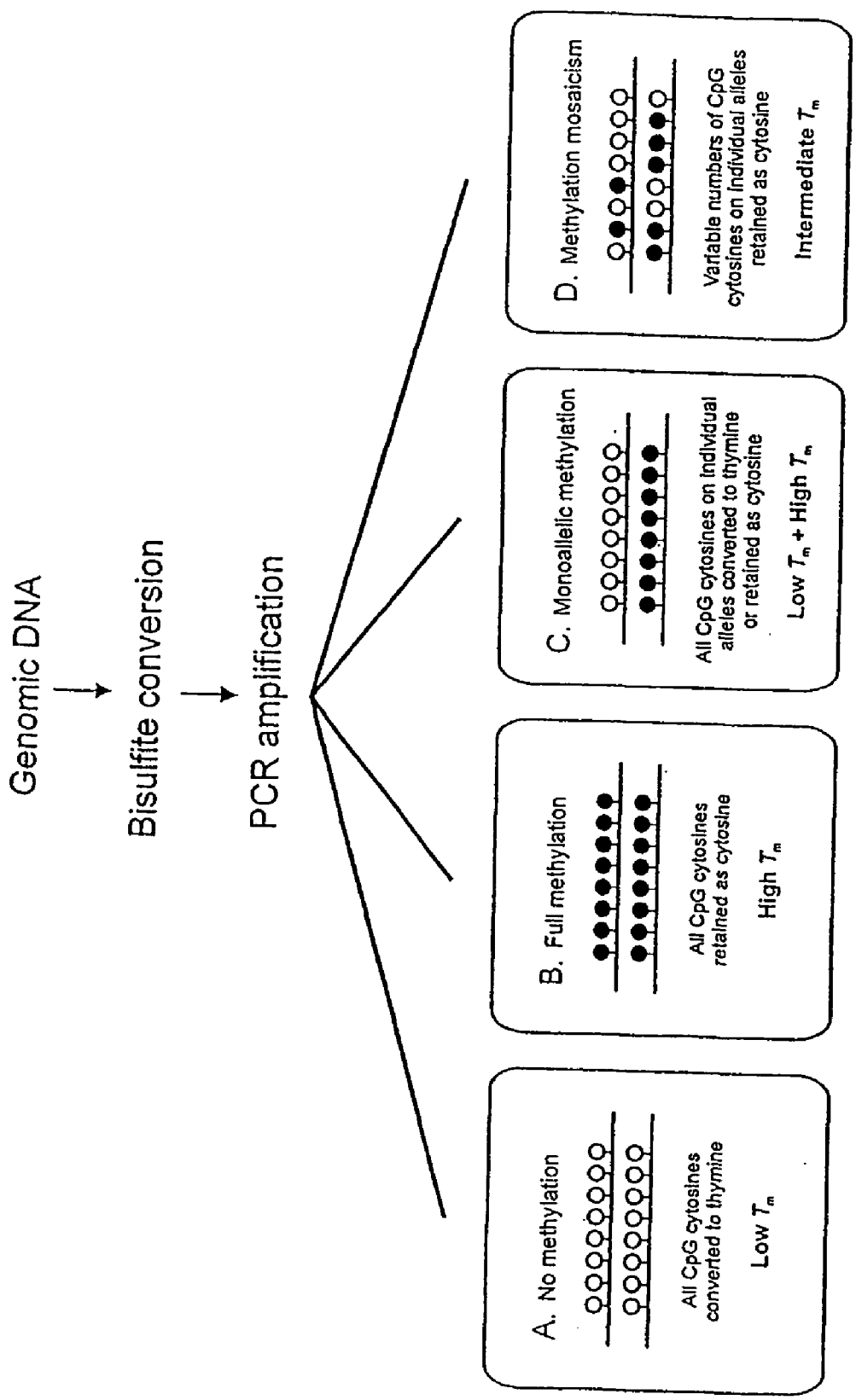
FIG. 1 shows principle of melting curve analysis for resolution of DNA methylation patterns.

Following conversion of unmethylated cytosines to uracil by sodium bisulfite and subsequent PCR-mediated conversion of uracils to thymine, methylated and unmethylated alleles are predicted to differ in thermal stability due to their different GC contents (Guldberg et al., 1998). The primary reason for the dependence of $T_m$ on GC content is that a G:C base pair contains three hydrogen bonds and is more stable than an A:T base pair, which contains only two hydrogen bonds). FIG. 1 shows schematically how the $T_m$ of an amplification product is determined by the composition of methylated and unmethylated alleles in the original DNA sample. If all alleles are completely devoid of $m^5C$, all cytosines will be converted to thymine, yielding a PCR product with a relatively low $T_m$ (FIG. 1A). By contrast, if all alleles contain $m^5C$ at all CpG dinucleotides, the $T_m$ of the PCR product will be significantly higher (FIG. 1B). In case the DNA sample contains a mixture of alleles that are either unmethylated or fully methylated, amplification will yield two different PCR products with a low and a high $T_m$, respectively (FIG. 1C). Finally, if the target sequence exhibits methylation 'mosaicism', i.e., the number of $m^5Cs$ varies among different alleles within the same sample, the PCR product represents a pool of molecules with different $T_m$s, resulting in an overall intermediate $T_m$ (FIG. 1D).

To allow optimal resolution of $T_m$ differences, it is important to consider the melting properties of the DNA sequence. As described below, the $T_m$ of a DNA sequence is not merely a function of the content of A:T and G:C base pairs.

DNA Melting Theory

In aqueous solutions kept at a temperature below 60° C., DNA takes a double-stranded, helical conformation maintained by hydrogen bonds between base pairs on opposite strands and stacking interactions between neighbouring bases on the same strand. When the temperature is raised abruptly, the two strands come apart and take a single-stranded, random coil conformation. This helix-to-random chain transition is termed "DNA melting" and may also be induced by chemical denaturants. Because the forces holding a DNA helix include both base pairing and stacking interactions, the melting temperature ($T_m$) of a DNA molecule is determined by the overall sequence, not just the GC content.

When a DNA molecule is subjected to gradual heating, it melts in a series of steps where each step represents the melting of a discrete segment, termed a "melting domain" (Abrams and Stanton, 1992). A DNA molecule may contain several melting domains, each consisting of 25-300 contiguous base pairs, with $T_m$s generally in the range of 60-90° C. Each domain may contribute to a peak in a differential hyperchromicity profile measured by ultraviolet absorbance (20). The domain that melts at the lowest temperature is referred to as the "lowest-melting domain"; the most stable domain is the "highest-melting domain".

Theoretical Prediction of DNA Melting Properties (Melting Maps)

The MELT87 and MELT94 programs, written in the laboratory of Leonard Lerman (Lerman L S. Silverstein K: Computational simulation of DNA melting and its application to denaturing gradient gel electrophoresis. Methods Enzymol 1987; 155: 482-501; and Lerman L S, Silverstein K. Fripp B, Sauer P, Dresselhaus C.—http://web.mit.edu/osp/www/melt-.htm), generate the melting map for a known DNA sequence, i.e., a plot of the midpoint temperature at which each base pair of the sequence is in 50:50 equilibrium between the helical and melted configurations. These programs use the Fixman-Friere modification of Poland's algorithm for DNA melting. Each melting domain of the DNA fragment appears as a horizontal line and is usually clearly demarcated from the adjacent domains on either side. Modified versions of the MELT programs are commercially available (for example the MacMELT™ program from Bio-Rad, but may not provide the facilities for calculating the rate of strand dissociation (bimolecular melting; see below). The MELT program is highly useful for predicting the domain pattern of a DNA molecule, but not for predicting $T_m$(Abrams and Stanton, 1992).

Unimolecular Versus Bimolecular DNA Melting

The melting map generated with the MELT program represents only the unimolecular component of DNA melting and therefore applies only at indefinitely high DNA concentrations. At experimentally relevant concentrations, the bimolecular component of DNA melting will become significant, resulting in complete dissociation of the DNA strands at a temperature below the melting of the highest domain, as indicated by the melting map. The rate of strand dissociation is determined by the equilibrium constant of dissociation at a given temperature, which may be estimated by using the MELT program. The temperature of strand dissociation may be elevated by the attachment of a GC-clamp (Myers et al., 1985).

Fragment Design

To resolve differences in methylation content, primer pairs must be designed carefully to ensure optimal PCR amplification and optimal melting behaviour of the amplified product. While there are no strict rules that should be followed when designing experiments, and while differences in methylation status may be detected even under sub-optimal conditions, the following guidelines are recommended for optimal performance:

I. Assure that the difference in $T_m$ between the methylated and unmethylated sequence is sufficiently high to allow resolution by melting curve analysis.

II. Assure that the entire sequence to be analysed is contained within one lower-melting domain (for both unmethylated and methylated sequences).

III. Assure that the temperature of strand dissociation is higher than the melting temperature of the melting domain of interest.

IV. Assure that the primers amplify only fully bisulfite-converted DNA and do not discriminate between methylated and unmethylated alleles.

V. Assure that the primers do not discriminate between methylated and unmethylated alleles at the amplification level.

Re point I. The $T_m$ of the amplified sequence correlates broadly with the number of methylated sites in the original template. Although a difference of only one $m^5C$ may cause a $T_m$ difference (see below), a limitation is the variation inherent with the machine. Ideally, the number of CpG sites (or other methylated cytosines) in the target sequence must be high enough to generate non-overlapping melting peaks, even at relatively high temperature transition rates.

Re point II. Multiple melting domains in a PCR product result in a corresponding number of melting peaks, provided that strand dissociation is negligible, which may significantly disturb the readout. Furthermore, a change in the methylation status of a particular CpG dinucleotide will affect only the $T_m$ of the melting domain in which the CpG is located. Preferably, all CpG sites of the target region should be contained in one lower-melting domain of the amplified product. Modulation of melting profiles may be effectively achieved by PCR-based GC-clamping (Sheffield et al., 1989).

Re point III. An example is shown below of how the readout may be significantly disturbed if strand dissociation becomes significant, and how the temperature of strand dissociation may be elevated by increasing the length of the GC-clamp.

Re point IV. For design of primers, the guidelines given by Clark et al (Clark et al., 1994) should generally be followed. Preferably the primers should be designed to DNA regions completely devoid of CpG dinucleotides, be relatively long (typically 25-30 bp) due to the low GC-content of the template, and show limited internal complementarity and limited complementarity between primer pairs. Especially in CpG islands, it may not be possible to find identify CpG-free regions. In this case, the primers must contain a minimum of CpG, and a mismatch to both the methylated and unmethylated sequence must be incorporated at the C residue of the CpG dinucleotide (Clark et al., 1994). The purity of the amplified product may be improved by nested PCR (Clark et al., 1994).

Re point V. Unmethylated and methylated DNA sequences differ in GC content after treatment with bisulfite. A pitfall inherent with the analysis of bisulfite-treated DNA is therefore that the two species are not amplified with equal efficiency, resulting in a significant bias (Warnecke et al., 1997). At present, there are no general rules available to avoid such PCR bias, which should therefore be excluded experimentally by analysing a sample containing both methylated and unmethylated DNA, preferably in a ratio of 1:1.

Requirement for GC-Clamping

Figure 6:
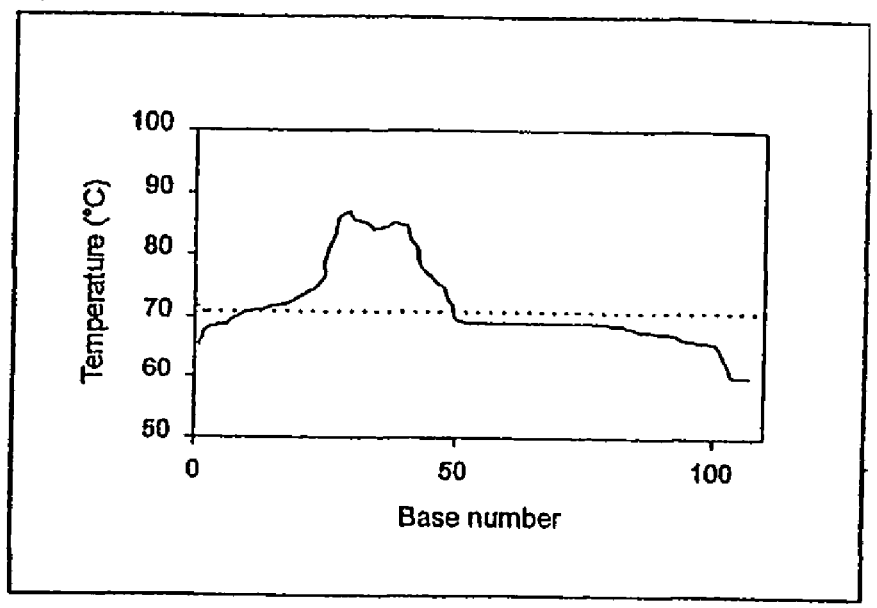
FIG. 6 shows the melting transition for a 107-bp region of the MDR1 gene (FIG. 6A). The solid line in the melting map represents the unimolecular component of DNA melting for the upper DNA strand in the fully methylated configuration (all cytosines in CpG dinucleotides are methylated). The dashed line in the melting map indicates the equivalent temperature at which the calculated strand dissociation constant is $10^{-6}$ M, as calculated by MELT94, i.e., the temperature at which strand dissociation is probable. PCR-mediated attachment of a GC-clamp to the sequence of interest is shown in FIG. 6B.
Figure 6:
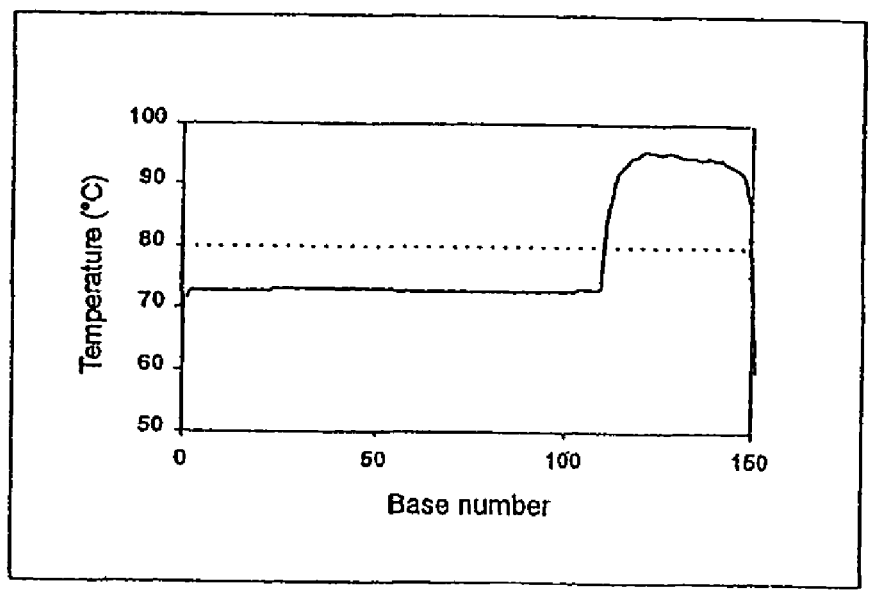

As described above, both the unimolecular and bimolecular components of DNA melting may become significant at experimental relevant DNA concentrations. An example of how this may influence the melting transition is shown for a 107-bp region of the MDR1 gene (FIG. 6A). The solid line in the melting map represents the unimolecular component of DNA melting for the upper DNA strand in the fully methylated configuration (all cytosines in CpG dinucleotides are methylated). The dashed line in the melting map indicates the equivalent temperature at which the calculated strand dissociation constant is $10^{-6}$ M, as calculated by MELT94, i.e., the temperature at which strand dissociation is probable. The correspondence between theory and experimental data have been thoroughly documented (Myers et al., 1985). Two features of this melting map are significant. First, the 107-bp fragment has two main melting domains differing by about 9° C. Second, strand dissociation occurs at a temperature that is higher than the $T_m$ of the lower-melting domain, but lower than the $T_m$ of the higher-melting domain. Accordingly, the higher-melting domain should remain in the double-stranded configuration during the melting of the lower-melting domain, but strand dissociation occurs at a slightly higher temperature (<1° C.). Because each of these transitions results in a melting peak, melting analysis of this fragment would result in a composite profile consisting of two melting peaks with a small difference in $T_m$. This has two disadvantages: first, interpretation of the data is severely hampered, and second, differences in methylation content in the higher-melting domain may remain unresolved (Myers et al., 1985; Abrams and Stanton, 1992).

PCR-mediated attachment of a GC-clamp to the sequence of interest serves two purposes, which are exemplified in FIG. 6B. First, GC-clamping can be used to convert the entire sequence of interest into a single lower-melting domain (for both unmethylated and methylated sequences). Second, it can be used to increase the temperature of strand dissociation to far above the $T_m$ of the melting domain containing the sequence of interest. For some amplified sequences, the temperature at which strand dissociation occurs may be lower than the temperature at which unimolecular melting occurs. In such cases, GC-clamping may not be necessary.

Materials and Methods

DNA Samples

Mononuclear cells were obtained from peripheral blood from healthy individuals and patients with Angelman syndrome or Prader-Willi syndrome, or from bone marrow from patients with acute myeloid leukemia (AML). Cutaneous malignant melanomas were snap frozen in liquid nitrogen immediately after surgery and stored at −80° C. until use. Genomic DNA was isolated using the Puregene DNA Isolation Kit (Gentra Systems). DNA from the leukemia cell lines, MOLT-4 and HL-60, served as positive and negative control for $p15^{Ink4b}$ methylation, respectively (11). Universally methylated DNA was generated by treating genomic DNA isolated from normal peripheral blood mononuclear cells with Sss I methyltransferase (New England Biolabs), according to manufacturer's instructions. Blood and bone marrow samples were obtained after informed consent, and all procedures were in accordance with the current revision of the Helsinki Declaration of 1975.

Sodium Bisulfite Conversion

Genomic DNA was treated with sodium bisulfite essentially as described previously (12, incorporated herein by reference). Briefly, approximately 2 μg of DNA were denatured in 0.3 M NaOH for 15 min at 37° C., followed by the addition of sodium bisulfite to a final concentration of 3.1 M, and hydroquinone to a final concentration of 2.5 mM. After incubation at 55° C. for 16 h, the DNA samples were recovered by using the GeneClean II Kit (Bio 101 Inc.), desulphonated in 0.3 M NaOH, and ethanol-precipitated. DNA was resuspended in TE and used immediately or stored at −80° C. until use Primer Design and PCR Amplification Melt maps were generated by using the MELT94 program (13). Primers specific for bisulfite-converted antisense strand DNA were selected to amplify a region of the small nuclear ribonucleoprotein-associated polypeptide N gene (SNRPN) promoter CpG island (GenBank accession L32702, bases 153-305). This region is within the area known to be differentially methylated in the Angelman and Prader-Willi syndromes (14). The primers were

[SEQ ID NO. 1]
SNRPN-A
[CGGGCGGGGGI-CATACTCARACTARAATATATACTAAACCTACC
and

[SEQ ID NO. 2]
SNRPN-B
[CGCCCGCCGCGCCCCGCGCCCGTCCCGCCCCCCGCCCG]-

AGAGAAGTTBTIGGTATAGTTGATTTTGTT.

Primers for amplification of the sense strand of the APC promoter 1A CpG island (Genbank accession U02509) were

[SEQ ID NO. 3]
[CGCC] TGCGAGGGGTTTTGTGTTTTATT (APC-MC-A)
and

[SEQ ID NO. 4]
CGCCCGCCGCGCCCCGCGCCCGTCCCGCCGCCCCCGCCCG]-

CCATTCTATCTCCAATAACACCCTAA (APC-MC-B).

brackets represent GC-clamps. Primers for amplification of the $p15^{Ink4b}$ promoter CpG island were as described previously (11). PCR was carried out in a final volume of 25 μl containing 100-200 ng of bisulfite-treated DNA, 10 mM Tris-HCl (pH 8.3), 50 mM KCl, 1.5 mM $MgCl_2$, 0.2 mM dNTP, 0.4 μM each primer, and 1 U of AmpliTaq polymerase (Perkin-Elmer). PCR was initiated by hot-start, followed by 39 cycles of 94° C. for 30 s, 55° C. for 30 s and 72° C. for and a final extension at 72° C. for 5 min, using a block thermocycler (GeneAmp PCR System 9600; Perkin-Elmer). PCR products were examined by electrophoresis on 2-3% agarose gels (FMC).

For amplification on the LightCycler (Roche Molecular Biochemicals), a LightCycler DNA Master SYBR Green I kit (Roche Molecular Biochemicals) was used. Prior to amplification, 2 μl of 10× LightCycler DNA Master SYBR Green I were mixed with 0.16 μl of TaqStart Antibody (Clontech) and incubated at room temperature for 5 min. PCR was performed in 20-μl reactions containing 2 μl of 10× LightCycler DNA Master SYBR Green I, 3 mM $MgCl_2$ (final concentration), 200 ng of bisulfite-treated DNA and 0.5 μM each primer. PCR was initiated by incubation for 1 min at 95° C. to denature the TaqStart Antibody, followed by 40-50 cycles of 5 s at 95° C., 10 s at 55° C. and 15 s at 72° C. The fluorescence of SYBR Green I was measured once each cycle to monitor template amplification.

Generation of Melting Curves and Melting Peaks

DNA melting curves were acquired on the LightCycler by measuring the fluorescence (F) of SYBR Green I during a linear temperature transition from 70° C. to 100° C. at 0.1° C./s. Fluorescence data were converted into melting peaks by using the LightCycler software (version 3.39) to plot the negative derivative of fluorescence over temperature versus temperature (−dF/dT vs T). For PCR products generated on a block thermocycler, 5 μl of PCR product were mixed with 10:1 of 1.5×PCR buffer and 5 μl of a 1:5,000 dilution of SYBR Green I (Molecular Probes), 5 μl of a 1:1,250 dilution of Picogreen (Molecular Probes), or 5 μl of a 1:1,250 dilution of ethidium bromide (Sigma) prior to melting curve analysis. Unless otherwise stated, melting curve analysis was performed in the presence of SYBR Green I. For PCR products generated on the LightCycler, melting curve analysis was performed immediately after amplification.

Results
Rationale of Melting Curve Analysis for DNA Methylation Profiling

When a double-stranded DNA molecule is subjected to gradual heating, it melts in a series of steps where each step represents the melting of a discrete segment, a so-called 'melting domain'. In general, the $T_m$ of a melting domain increases with an increase in GC content. Following conversion of unmethylated cytosines to uracil by sodium bisulfite and subsequent PCR-mediated conversion of uracils to thymine, methylated and unmethylated alleles are predicted to differ in thermal stability due to their different GC contents (15).

FIG. 1 shows schematically how the $T_m$ of an amplification product is determined by the composition of methylated and unmethylated alleles in the original DNA sample. If all alleles are completely devoid of $m^5C$, all cytosines will be converted to thymine, yielding a PCR product with a relatively low $T_m$ (FIG. 1A). By contrast, if all alleles contain $m^5C$ at all CpG dinucleotides, the $T_m$ of the PCR product will be significantly higher (FIG. 1B). In case the DNA sample contains a mixture of alleles that are either unmethylated or fully methylated, amplification will yield two different PCR products with a low and a high $T_m$, respectively (FIG. 1C). Finally, if the target sequence exhibits methylation 'mosaicism', i.e. the number of $m^5Cs$ varies among different alleles within the same sample, the PCR product represents a pool of molecules with different $T_m$s, resulting in an overall intermediate $T_m$ (FIG. 1D).

In-Tube Melting Curve Analysis of the SNRPN Gene

The gene encoding small nuclear ribonucleoprotein-associated polypeptide N (SNRPN) is a convenient model for investigating melting profiles of different allelic constellations of DNA methylation. SNRPN is located in an imprinting regulatory region at chromosome 15q11-q13, and its promoter is usually fully methylated (>96% of all CpG dinucleotides) on the maternal chromosome and completely devoid of methylation on the paternal chromosome (14). Two inherited developmental disorders, Prader-Willi syndrome and Angelman syndrome, are caused by large deletions, uniparental disomy or imprinting mutations of the SNRPN region. While normal individuals have both methylated and unmethylated SNRPN alleles, patients with Prader-Willi syndrome have only methylated alleles and patients with Angelman syndrome have only unmethylated alleles (16).

Figure 2:
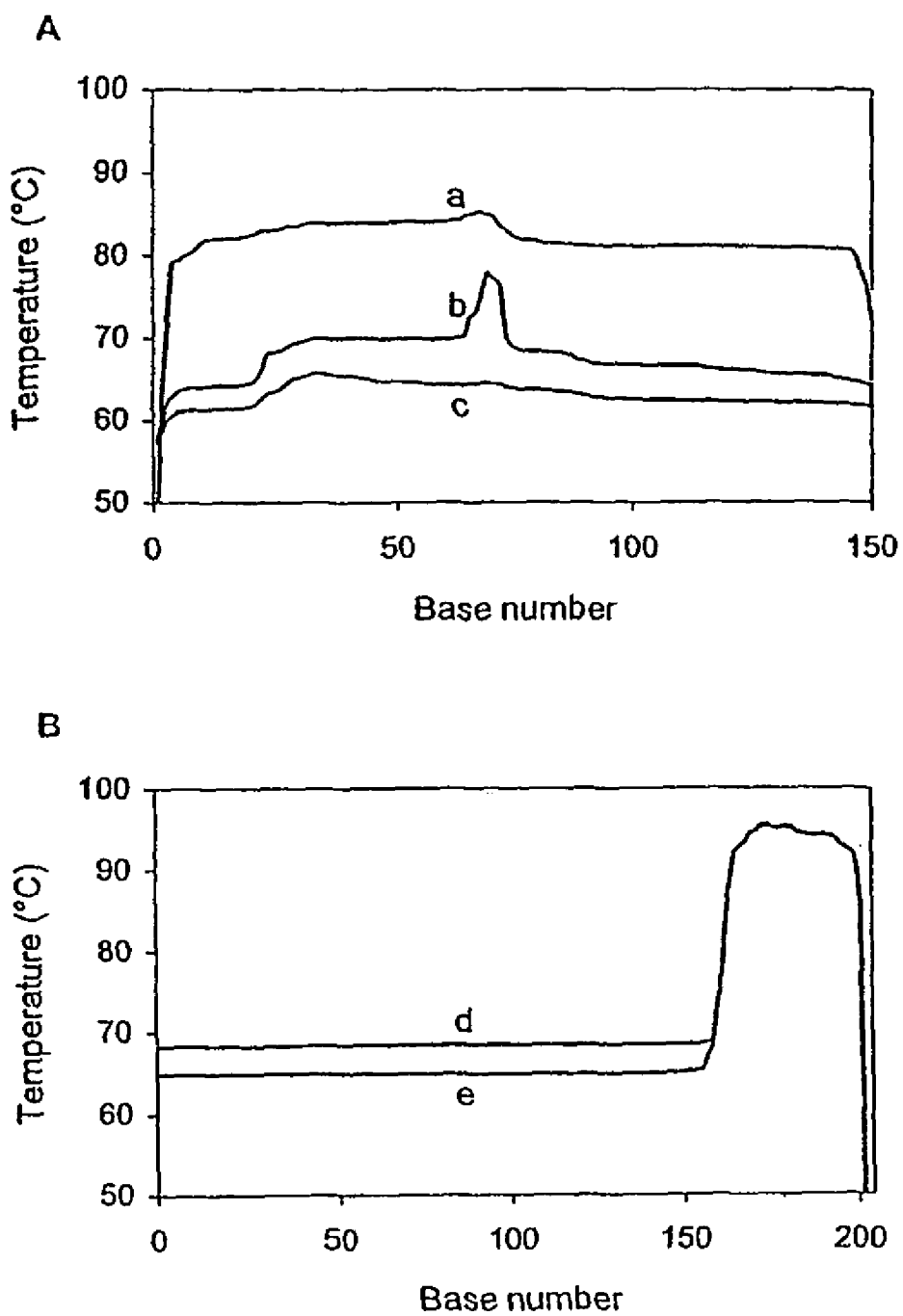
FIG. 2 shows (A) Computerized melt maps of a 153-bp region of the SNRPN promoter in untreated genomic DNA (curve 'a') and DNA after treatment with sodium bisulfite (curve 'b', methylated lower strand; curve 'c', unmethylated lower strand). (B) Melt maps calculated for the 203-bp GC-clamped SNRPN PCR product (curve 'd', methylated; curve 'e', unmethylated).

FIG. 2A depicts the melt map of a 153-bp genomic DNA region of the SNRPN CpG island, including 11 CpG dinucleotides. This region has a GC content of 67% with a predicted maximum $T_m$ of 85° C. Treatment with sodium bisulfite and subsequent PCR would result in the formation of two distinct noncomplementary strands with GC contents and $T_m$s determined by the $m^5C$ contents of the original templates. For the antisense strand, the fully methylated sequence would have a GC content of 33% and a maximum $T_m$ of 70° C., while the unmethylated sequence would have a GC content of 26% and a maximum $T_m$ of 66° C. (FIG. 2A).

DNA samples from a normal individual, a patient with Prader-Willi syndrome and a patient with Angelman syndrome were treated with sodium bisulfite, and the SNPRN promoter CpG island was subsequently amplified and GC-clamped with primers that are specific for bisulfite-treated DNA but do not discriminate between methylated and unmethylated alleles. The melt maps of the amplification products originating from either methylated or unmethylated SNPRN alleles are depicted in FIG. 2B. The GC-clamped sequence containing the unmethylated SNRPN region has a lower-temperature melting domain with a predicted $T_m$ of 64.9° C., whereas the $T_m$ of this domain is 68.3° C. for the fully methylated sequence (FIG. 2B) By conventional PCR, all samples yielded a product of the expected length and no unintended products (not shown).

Figure 3:
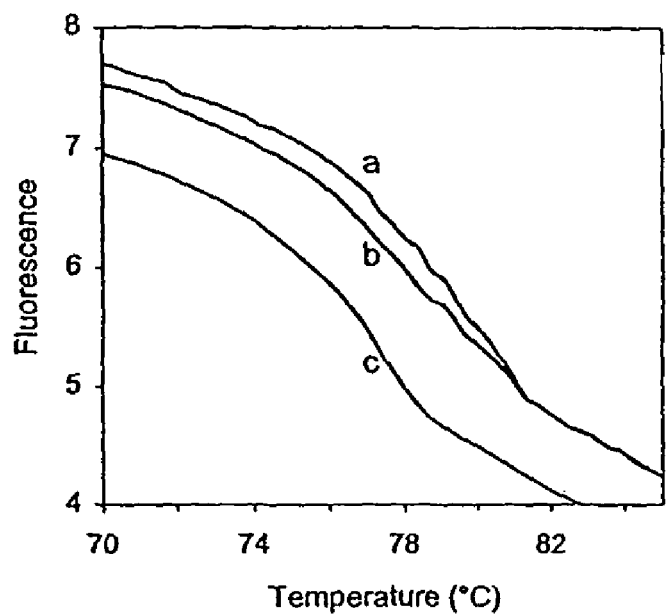
FIG. 3 shows fluorescence melting curves (A) and melting peaks (B) for the SNRPN gene. Bisulfite-treated DNA was amplified from a patient with Prader-Willi syndrome (curves 'a'), a normal individual (curves 'b') and a patient with Angelman syndrome (curves 'c'). Fluorescence data for melting curves were acquired by heating the PCR products from 70° C. to 98° C. at a transition rate of 0.1° C./s in the presence of SYBR Green I. Melting peaks were obtained by plotting the negative derivative of fluorescence over temperature versus temperature (−dF/dT vs T).
Figure 3:
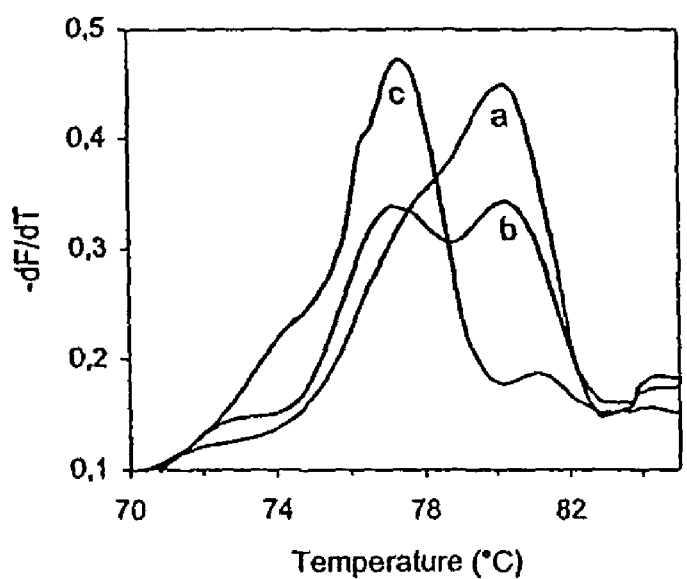

Melting analysis of the three PCR products showed a mono- or biphasic decrease in the fluorescence (F) of the double stranded DNA dye SYBR Green I (FIG. 3A). When the melting curves were converted to melting peaks by plotting the negative derivative of fluorescence over temperature versus temperature ($-dF/dT$ vs $T$), the three samples were easily differentiable (FIG. 3B). With bisulfite-treated DNA from a patient with Angelman syndrome, a single melting peak was observed with an apparent $T_m$ of 77.4° C., whereas a single peak with an apparent $T_m$ of 80.3° C. was obtained with DNA from a patient with Prader-Willi syndrome. With DNA from a normal individual, two melting peaks were observed with apparent $T_m$s of 77.3° C. and 80.3° C., respectively (FIG. 3B).

To test the reproducibility of this method, the inventors used the SNRPN model to examine inter-tube and inter-sample variability. When the same SNRPN PCR product generated from DNA from a normal individual was distributed among seven individual glass capillaries, the $T_m$ varied by approximately 0.3° C. for both the unmethylated peak and the methylated peak. The variation in $T_m$ was approximately 0.4° C. when the same DNA template was amplified in seven independent reactions and subjected to melting curve analysis. In an additional series of experiments with DNA from four different individuals the $T_m$ variation was less than 0.6° C. and the average $T_m$ did not vary between experiments performed on different days. These data suggest that the melting peak data are highly reproducible under fixed assay conditions, and that the subtle variations in $T_m$ can be ascribed, at least in part, to temperature differences in the sample carrousel, in agreement with the technical specification of the LightCycler system (LightCycler Operator's Manual, Ver. 3.0). Initial heating and reannealing prior to melting profiles, probably due to the formation of heteroduplexes and/or hybrids between amplified DNA and excess primers (data not shown).

In-Tube Detection of Heterogeneous Methylation Patterns

Figure 5:
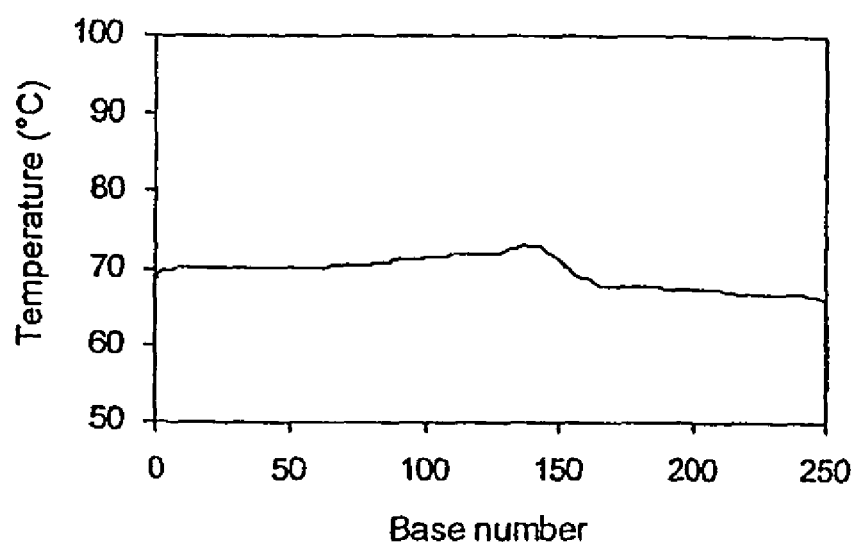
FIG. 5 relates to the second aspect of the present invention.
Figure 5:
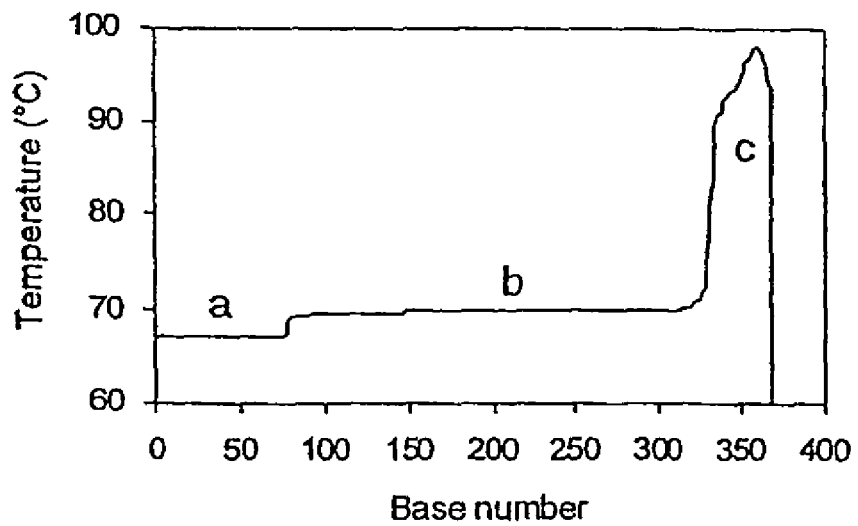

To examine the feasibility of resolving heterogeneous methylation patterns by melting curve analysis, the present inventors examined the promoter CpG island of the p15$^{Ink4b}$ tumor suppressor gene, which displays a high degree of intra- and interindividual variation in methylation density among patients with acute myeloid leukemia (AML) (11;17). Bisulfite-treated DNA from AML patients and control cell lines was amplified and GC-clamped with primers flanking a region of p15$^{Ink4b}$ that contains 27 CpG dinucleotides (11). As shown in FIG. 5, DNA from the unmethylated cell line HL-60 showed a melting peak with an apparent $T_m$ of 81.3° C., whereas a peak with an apparent $T_m$ of 88.9° C. was obtained with DNA from the methylated MOLT-4 cell line. With DNA from two AML samples previously shown to contain high fractions of heterogeneously methylated p15$^{Ink4b}$ alleles (11), melting transitions tended to broaden and the melting peaks had $T_m$s of 84.4° C. and 86.2° C., respectively. Thus, in accordance with the theory (FIG. 1D), samples containing heterogeneously methylated DNA show melting peak $T_m$ values between those of the corresponding unmethylated and fully methylated sequences.

When melting curve acquisition was integrated with PCR on the LightCycler by using the components from a commercial kit, the p15$^{Ink4b}$ melting peak profiles of HL-60 and MOLT-4 were similar to those obtained with PCR products generated on a block thermocycler (data not shown). However, the melting peaks shifted significantly ($T_m$=83.6° C. for HL-60 and $T_m$=92.4° C. for MOLT-4), possibly due to the different concentrations of $MgCl_2$ and the substitution of dTTP with dUTP.

Examples

This section contains examples of the different aspects of the present invention. The experimental examples have been divided into five categories, as follows. Examples of "basic" assays for distinguishing between methylated and unmethylated DNA sequences (A); examples of detecting aberrant DNA methylation in human inherited disorders (B); examples of detecting aberrant methylation in human tumours (C); examples of detecting small differences in the number of $m^5C$ (D); examples of detecting aberrant methylation using different double-stranded DNA binding dyes (E).

A. Resolution of DNA Methylation by Melting Curve Analysis

The two examples below show resolution of differential DNA methylation in human genes by means of PCR melting curve analysis. The standard procedure included I. Isolation of genomic DNA.
II. Treatment of genomic DNA with sodium bisulfite.
III. Generation of PCR products in a block thermal cycler.
IV. Analysis of the amplification products by agarose gel electrophoresis.
V. Melting curve analysis in the presence of the double-stranded DNA-binding fluorescent dye, SYBR Green I, using the LightCycler system.

In both cases, oligonucleotide primers for PCR amplification and GC-clamping were chosen on the basis of the general principles described in Section 5.4. DNA treated in vitro with Sss I methyltransferase was used as a positive control for methylated alleles (see point VI, below).

HIC1

To study the methylation status of the HIC1 gene (Accession No. NM_006497), primers were generated to amplify a 117-bp region (pos. 76-192) of the upper strand of bisulfite-treated DNA. Primer binding sites are doubly underlined. The 5'-end primer was extended with a 40-bp GC-clamp, and the 3'-end primer was extended with a 9-bp GC-clamp (shown in brackets). The region between the primer binding sites contains 9 CpG dinucleotide sites (singly underlined). The final amplification product is 166 bp.

[SEQ ID NO. 5]
5'[cgcccgccgcgcccgcgcccgtcccgccgccccgcccg]ataa ttagCGtattaagggttttttgtaCGUCGUCGtggtgtagaaCGttttttt CGCGCGtataagaaCGtgttggCGgttagtagCGtttattttaagttttt ggtgg[gccgcccgc]3'

Figure 7:
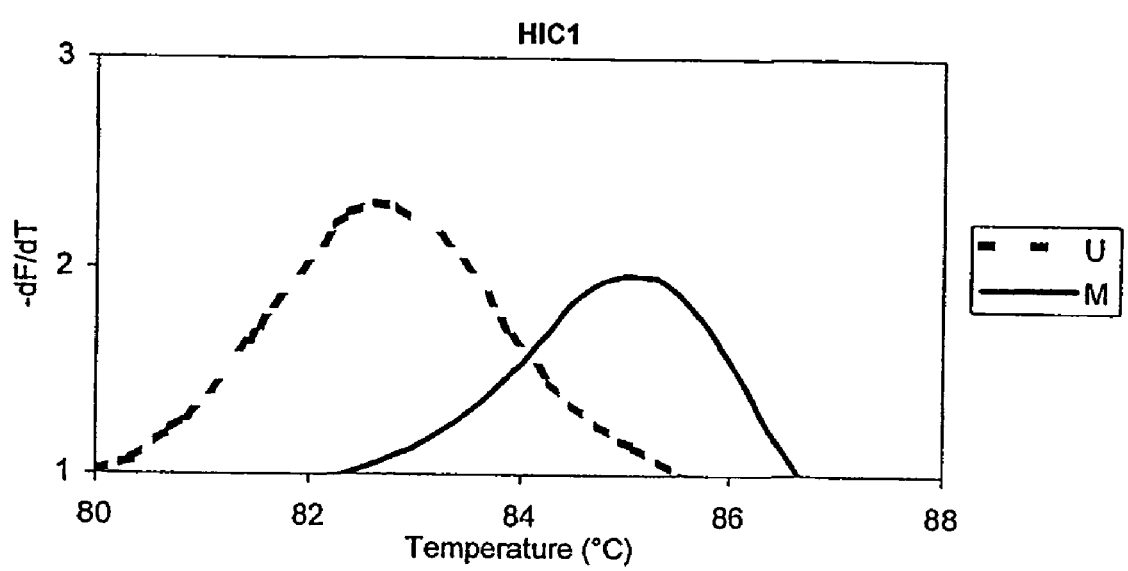
FIG. 7 shows fluorescence melting peaks for the HIC1 gene. Sss I-treated DNA (Curve 'M') and DNA from normal lymphocytes (curve 'U') was treated with sodium bisulfite and PCT amplified. The PCR products were mixed with SYBR Green I and subjected to melting analysis.

According to the melting maps generated by using the MELT94 algorithm, the lower-melting domain has a $T_m$ of 70.9° C. for the methylated sequence and 66.8° C. for the unmethylated sequence. Sss I-methylated DNA and DNA from normal peripheral blood lymphocytes was treated with sodium bisulfite and amplified with the above primer pair. Both DNA samples yielded a product of the expected length and no nonspecific products. The PCR products were mixed with SYBR Green I and subjected to melting analysis. When the melting curves were converted to melting peaks by plotting the negative derivative of fluorescence over temperature versus temperature (−dF/dT vs T), a single melting peak with an apparent $T_m$ of 82.63° C. was observed with bisulfite-treated DNA from normal lymphocytes, and a single melting peak with an apparent $T_m$ of 84.97° C. was observed with bisulfite-treated, Sss I-methylated DNA (FIG. 7).

DAPK

To study the methylation status of the DAP-Kinase (DAPK) gene (Accession No. X76104), primers were generated to amplify a 103-bp region (pos. 17-119) of the upper strand of bisulfite-treated DNA. Primer binding sites are doubly underlined. The 5'-end primer was extended with a 40-bp GC-clamp, and the 3'-end primer was extended with a 5-bp GC-clamp (shown in brackets). The region between the primer binding sites contains 6 CpG dinucleotide sites (singly underlined). The final amplification product is 148 bp.

[SEQ ID NO. 6]
5'[cgcccgccgcgcccgcgcccgtcccgccgccccgcccg]

CgagttaaCGtCGgggattttgttttttttaCGgaggggattCGgtaatt

CGgtaattCGtagCGtagCGgtagggtttggggtCGgCG tttgggagggatttgCGttttttattt[ccgcc]-3'

Figure 8:
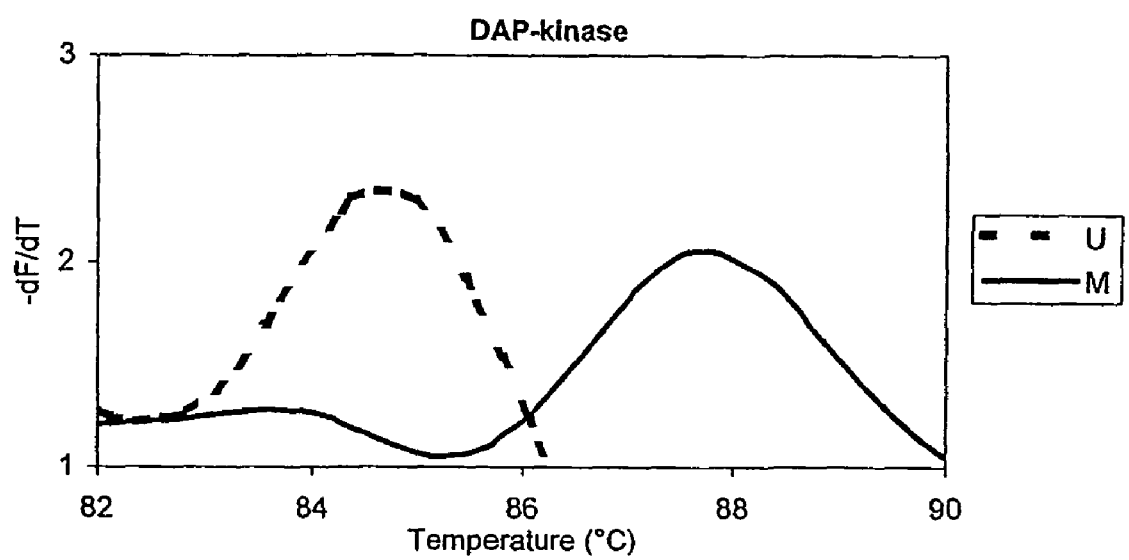
FIG. 8 shows fluorescence melting peaks for the DAPK gene. Sss I-treated DNA (curve 'M') and DNA from normal lymphocytes (curve 'U') was treated with sodium bisulfite and PCR amplified. The PCR products were mixed with SYBR Green I and subjected to melting analysis.

According to the melting maps generated by using the MELT94 algorithm, the lower-melting domain has a $T_m$ of 73.5° C. for the methylated sequence and 68.5° C. for the unmethylated sequence. Sss I-methylated DNA and DNA from normal peripheral blood lymphocytes was treated with sodium bisulfite and amplified with the above primer pair. Both DNA samples yielded a product of the expected length and no nonspecific products. The PCR products were mixed with SYBR Green I and subjected to melting analysis. When the melting curves were converted to melting peaks by plotting the negative derivative of fluorescence over temperature versus temperature (−dF/dT vs T), a single melting peak with an apparent $T_m$ of 84.63° C. was observed with bisulfite-treated DNA from normal lymphocytes, and a single melting peak with an apparent $T_m$ of 87.84° C. was observed with bisulfite-treated, Sss I-methylated DNA (FIG. 8).

B. Detection of Aberrant DNA Methylation in Human Inherited Disorders (Prader-Willi Syndrome and Angelman Syndrome)

The gene encoding small nuclear ribonucleoprotein-associated polypeptide N (SNRPN) is located in an imprinting regulatory region at chromosome 15q11-q13, and its promoter is usually fully methylated (>96% of all CpG dinucleotides) on the maternal chromosome and completely devoid of methylation on the paternal chromosome (Zeschnigk et al., 1997). Two inherited developmental disorders, Prader-Willi syndrome and Angelman syndrome, are caused by large deletions, uniparental disomy or imprinting mutations of the SNRPN region. While normal individuals have both methylated and unmethylated SNRPN alleles, patients with Prader-Willi syndrome have only methylated alleles and patients with Angelman syndrome have only unmethylated alleles (Nicholls et al., 1998).

To study the methylation status of the SNRPN gene (Accession No. L32702), primers were generated to amplify a 153-bp region (pos. 153-305) of the lower strand of bisulfite-treated DNA. Primer binding sites are doubly underlined. The 5'-end primer was extended with a 10-bp GC-clamp, and the 3'-end primer was extended with a 40-bp GC-clamp (shown in brackets). The region between the primer binding sites contains 11 CpG dinucleotide sites (singly underlined). The final amplification product is 203 bp.

[SEQ ID NO. 7]
3'[cgcccgccgc]gtatgagtttGCttttatatatGCtttggatgGC gatgatgttGCttagattGCgttttattttGCtgGCgGCttttatggatt GCgtagatagattttttGCtagttattGCGCtattttGCttgttttagtt gatatgGCtattgaagaga[cgcccgccgcgcccgcgcccgtcccgcc gccccgcccg]5' Pos. 305

According to the melting maps generated by using the MELT94 algorithm, the lower-melting domain has a $T_m$ of 68.3° C. for the methylated sequence and 64.9° C. for the unmethylated sequence. DNA samples from an apparently healthy individual, a patient with Prader-Willi syndrome and a patient with Angelman syndrome were treated with sodium bisulfite and amplified with the above primer pair (conditions described in section A). All DNA samples yielded a product of the expected length and no nonspecific products. The PCR products were mixed with SYBR Green I and subjected to melting analysis. When the melting curves were converted to melting peaks by plotting the negative derivative of fluorescence over temperature versus temperature (−dF/dT vs T), two melting peaks were observed with apparent $T_m$s of 77.3° C. and 80.3° C., respectively (FIG. 3A). With bisulfite-treated DNA from a patient with Angelman syndrome, a single melting peak was observed with an apparent $T_m$ of 77.4° C., whereas a single peak with an apparent $T_m$ of 80.3° C. was obtained with DNA from a patient with Prader-Willi syndrome (FIG. 3B).

C. Detection of APC Promoter Methylation in Solid Tumors (Malignant Melanoma)

The adenomatous polyposis coli gene (APC) is a tumor suppressor gene associated with both familial and sporadic cancers. Germline APC mutations are the cause of familial adenomatous polyposis (FAP), and somatic inactivation of APC by mutation or aberrant promoter methylation has been demonstrated in sporadic colorectal, gastric, breast and lung cancers. Dysfunction of APC leads to intracellular accumulation of β-catenin.

Figure 9:
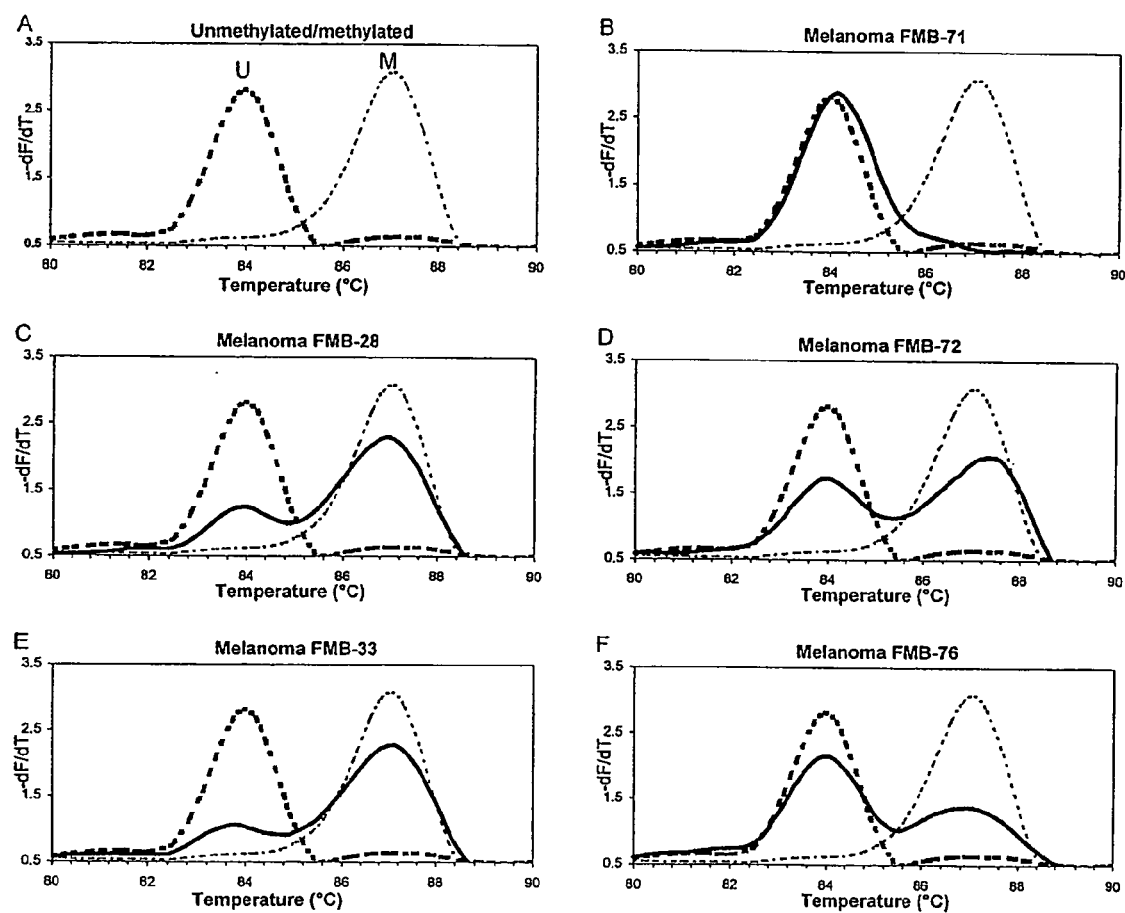
FIG. 9 shows fluorescence melting peaks for promoter 1A of the APC gene. Bisulfite-treated DNA from normal melanocytes (A) and melanoma biopsies (B-F) was amplified and subjected to melting curve analysis.

To investigate whether APC promoter methylation is responsible for aberrant accumulation of β-catenin in melanoma cells, the methylation status of APC promoter 1A was analyzed melting curve analysis in primary and metastatic tumors from patients with malignant melanoma. DNA from melanoma specimens was treated with sodium bisulfite and amplified with primers APC-MC-A and APC-MC-B. Bisulfite-treated DNA from normal melanocytes served as a positive control for unmethylated APC alleles, and a clone representing 14 m⁵Cs (see above) served as a positive control for methylated APC alleles. Examples of the subsequent melting curve analysis are shown in FIG. 9. Several melanoma samples displayed two distinct melting peaks (FIGS. 9C-F), corresponding to the peaks for unmethylated and fully methylated APC alleles, respectively. The height of the two peaks differed between the samples, probably reflecting different ratios of methylated and unmethylated APC alleles. The presence of methylated APC alleles in these samples was confirmed by methylation-specific PCR analysis (unpublished data). These data demonstrate that melting curve analysis can be used to detect DNA methylation in solid tumors, which contain significant amounts of normal, non-cancerous tissue.

D. Resolution of Small Differences in $m^5C$ Content

Figure 10:
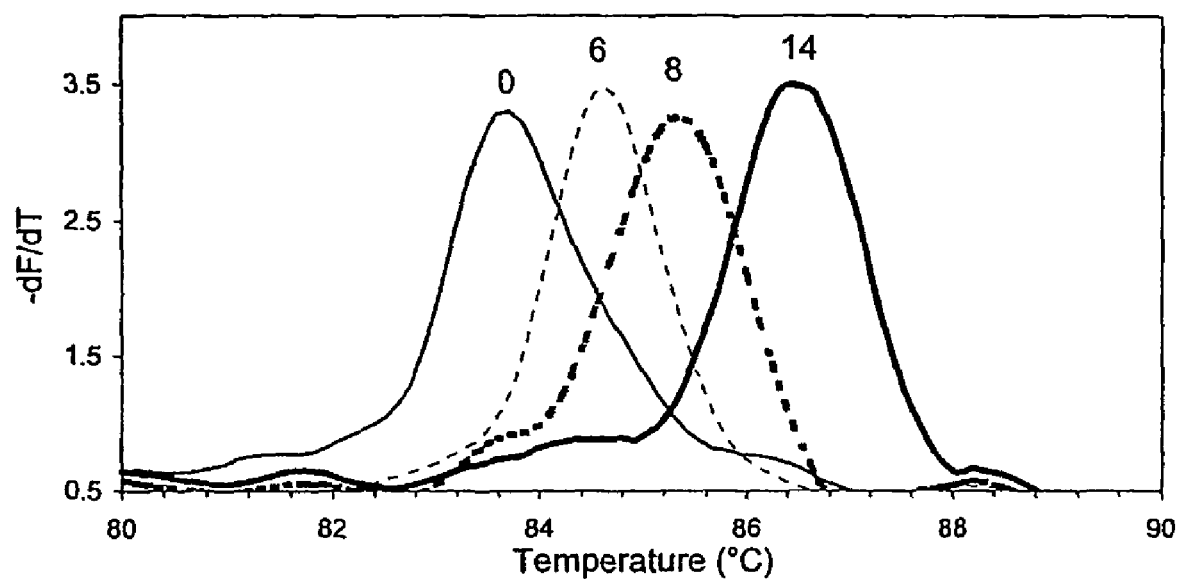
FIG. 10 shows fluorescence melting peaks for promoter 1A of the APC gene. Bisulfite-treated DNA from normal melanocytes (unmethylated, curve '0') and plasmid DNA representing 6, 8 and 14 methylated CpG sites (curves '6', '8' and '14') were amplified and subjected to melting curve analysis.

Two alleles differing by a single $m^5C$ differ by a single base pair (A:T versus G:C) after treatment with bisulfite. In theory, this difference in GC content causes a change in $T_m$, the magnitude of which is dependent on the length of the target sequence and the exact location of the base difference within the sequence. To test the sensitivity of the present invention, individually cloned PCR products corresponding to alleles carrying different numbers of $m^5C$ were analysed. Three clones of a PCR product generated from bisulfite-treated DNA from a melanoma cell line (FM91), which shows heterogeneous methylation of the APC promoter 1A (unpublished data), were amplified in the LightCycler using primers APC-MC-A and APC-MC-B. These primers generate a 240-bp PCR product covering 15 CpG sites in the APC promoter 1A. The same primers were used to amplify bisulfite-treated DNA from normal melanocytes, which show no evidence of APC promoter 1A methylation (unpublished data). Melting curve analysis of the amplified products revealed single melting peaks for all samples (FIG. 10). The apparent $T_m$ was 83.7° C. for the unmethylated control (melanoma cells), 84.7° C. for a clone representing 6 $m^5$Cs, 85.3° C. for a clone representing 8 $m^5$Cs, and 86.4° C. for a clone representing 14 $m^5$Cs. These data demonstrate that even small differences in $m^5C$ content can be resolved by melting curve analysis.

E. Alternative Double-Stranded DNA-Specific Dyes

A large number of fluorescent dyes alter their fluorescent properties when bound to double-stranded DNA. Ethidium bromide has moderate intrinsic fluorescence that increases 30-fold after binding to double-stranded DNA. Newer generation dyes, e.g. and PicoGreen and SYBR Green I, are essentially non-fluorescent when free in solution, but become highly fluorescent upon binding to double-stranded DNA.

Figure 11:
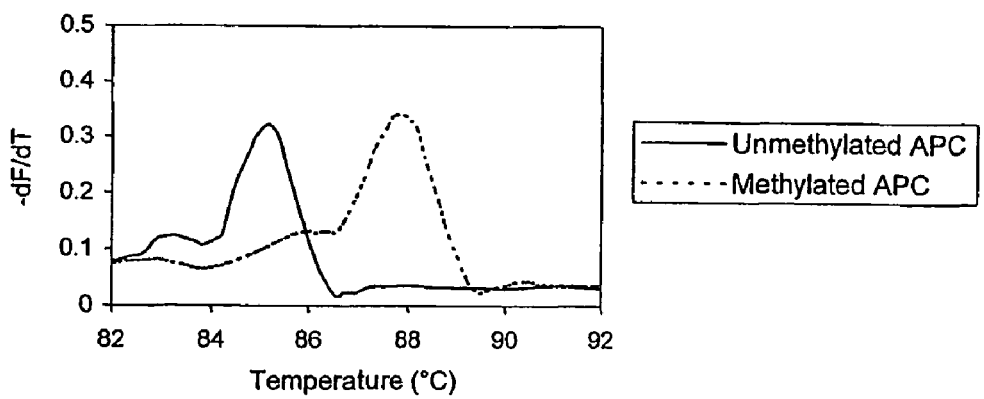
FIG. 11 shows fluorescence melting peaks for promoter 1A of the APC gene. Bisulfite-treated DNA from normal melanocytes ('unmethylated APC') and plasmid DNA representing 14 methylated CpG sites ('methylated APC') were amplified and subjected to melting curve analysis in the presence of ethidium bromide (A), PicoGreen (B) or SYBR Green I (C).
Figure 11:
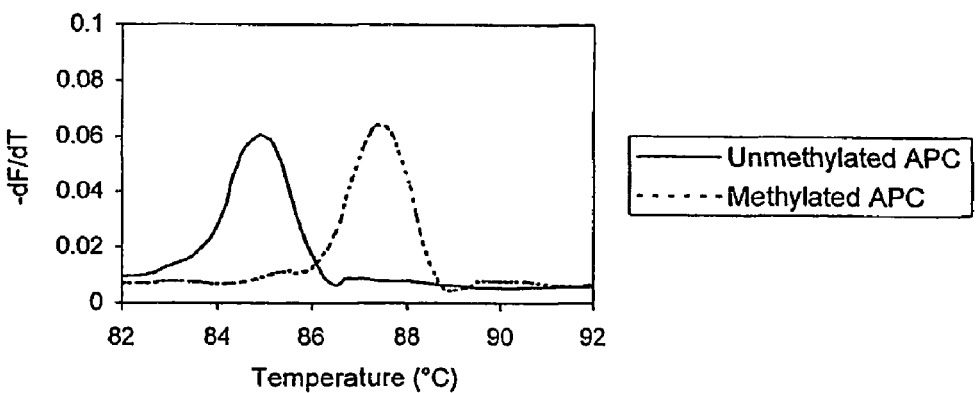
Figure 11:
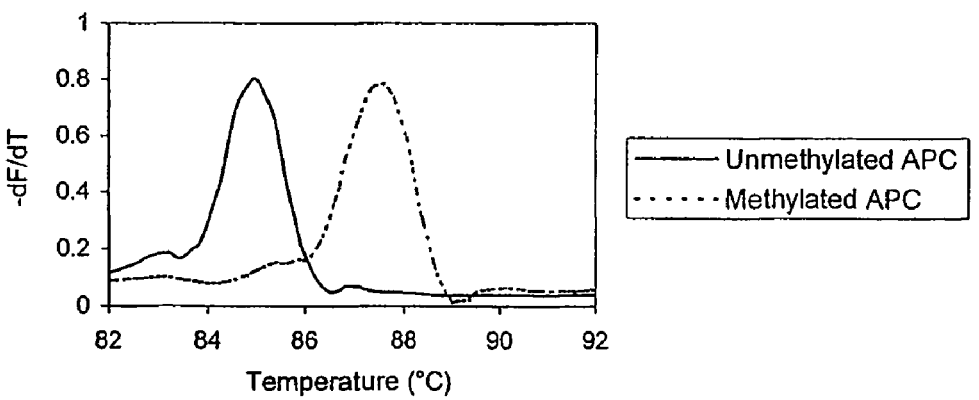

To study the applicability of different double-stranded DNA-specific dyes in the resolution of DNA methylation by melting curve analysis, Sss I-methylated DNA and DNA from normal peripheral blood lymphocytes was treated with sodium bisulfite and amplified with primers APC-MC-A and APC-MC-B to generate PCR products covering 15 CpG sites in the APC promoter 1A. Five microliters of the PCR products were mixed with 10 µl of 1.5×PCR buffer and 5 µl of a 1:5,000 dilution of SYBR Green I, 5 µl of a 1:1,250 dilution of PicoGreen, or 5 µl of a 1:1,250 dilution of ethidium bromide. DNA melting curves were acquired on the LightCycler by measuring the fluorescence of SYBR Green I, PicoGreen and ethidium bromide, respectively, and subsequently converted to melting peaks by plotting the negative derivative of fluorescence over temperature versus temperature (−dF/dT vs T). As shown in FIG. 11, all three dyes allowed resolution of methylated and unmethylated APC alleles, although the peaks generated with ethidium bromide (FIG. 11A) were less distinct than those generated with PicoGreen (FIG. 11B) or SYBR Green I (FIG. 11C). The apparent $T_m$s for unmethylated APC alleles were 84.42° C. with ethidium bromide, 84.88° C. with PicoGreen, and 84.95° C. with SYBR Green I. The corresponding $T_m$s for methylated APC alleles were 87.83° C., 87.39° C., and 87.49° C. These data demonstrate that different double-stranded DNA-specific dyes may be used to resolve DNA methylation by melting curve analysis.

Examples of Possible Instrumentation

Figure 12:
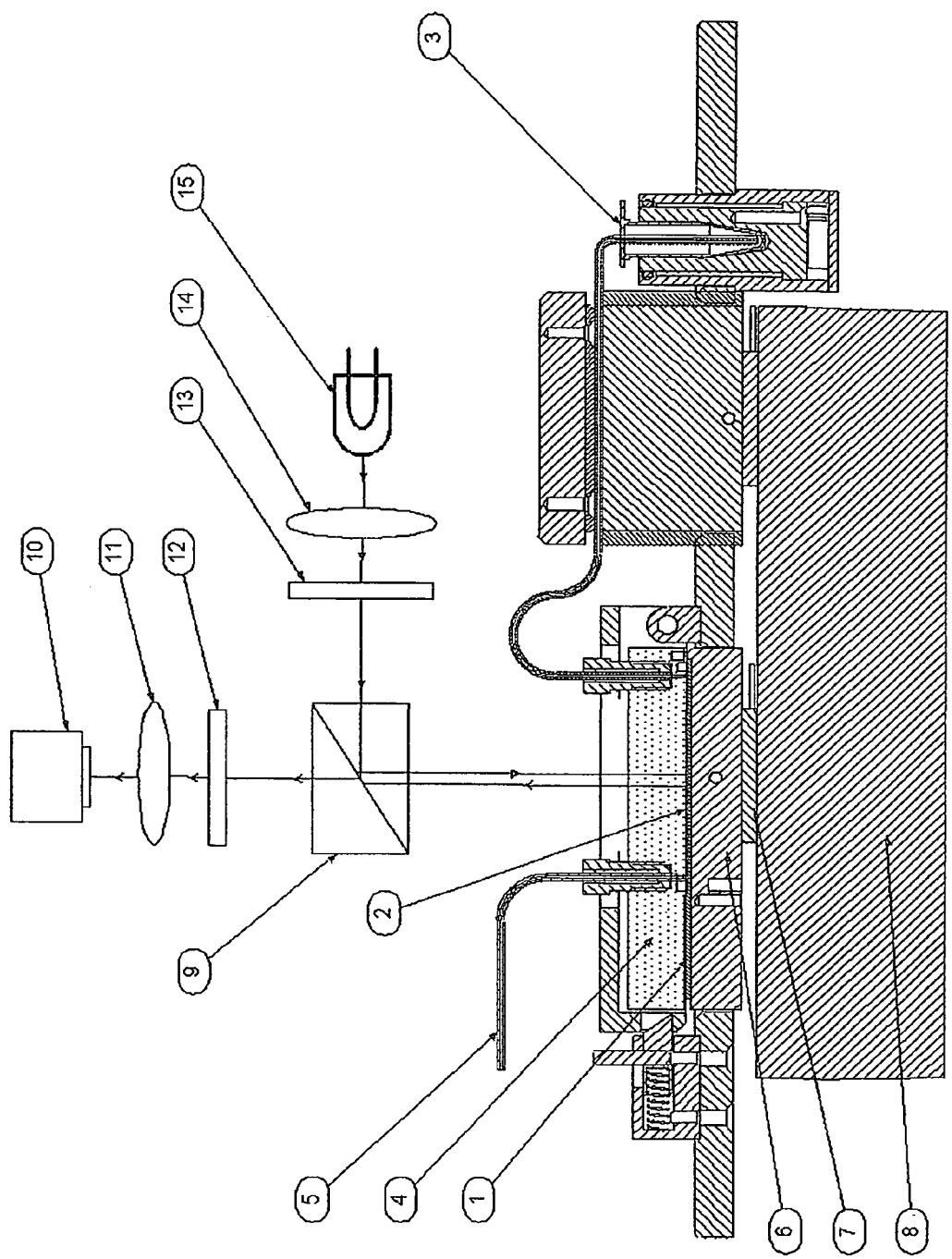
FIG. 12 shows an instrument to perform the melting assay on a glass slide format with immobilized PCR products.

FIG. 12 shows an instrument to perform the melting assay on a glass slide format with immobilized PCR products. The chamber is temperature controlled and the melting points of the PCR products can be measured by detecting the fluorescence signal at the location where they are immobilized. Using the CCD camera, multiple signals can be observed simultaneously. The numbering system used in the figure is as follows: 1. slide, 2. reaction chamber, 3. sample container, 4. chamber lid, 5. tube to syringe pump, 6. heating element, 7. peltier element, 8. heat sink, 9. radiation partitioner, 10. CCD camera, 11. reflection optics, 12. filter (for emission wavelength), 13. filter (for activation wavelength), 14. condenser optics, and 15. light source.

As mentioned above, the present invention may be carried out using a pre-prepared kit. The kit may comprises various elements required for carrying out the method of the first or second aspect of the invention. Those elements include the specific primers for the converted target nucleic acid in the first aspect of the invention or the test and control nucleic acid in the second aspect of the invention. In an embodiment of the present invention, one of these primers may be immobilised on a solid support such as a chip. Two examples are provided below illustrating this embodiment.

1. The amplification using the primers as described above is carried out using a polymerase chain reaction with one primer immobilized on a solid phase and the second primer in solution, adding a signal agent in a buffer. Preferably, an instrumental setup as described in FIG. 12 is used. At different locations of the solid surface different primers specific for different target nucleic acid sequences can be immobilized and therefore different known PCR products are synthesized at different known locations. The signal agent is again capable of providing a distinction between double-stranded and single stranded nucleic acids. The amount of intercalated signal agent decreases while the DNA is melting and this is measured simultaneously for a large part of the solid phase. The surface can be temperature controlled and an increase in temperature leads to a decrease in the fluorescence signal at the respective spot on the solid surface as a function of the melting of the DNA.

2. In a second example, the method is carried out in terms of measurement like the one described above but the immobilization of the PCR products is performed differently. Using this method, a large number of different PCR products from one or more samples are generated using two primers each. At least one of the primers of the respective pair is modified such that it can bind to the solid surface, for example with a thiol or amino-modification which is commercially available. Other specific binding members will be known to the skilled person, e.g. biotin/avidin, antibody/antigen or enzyme/ligand. Using a chip spotting device which is commercially available and known to the researcher skilled in the art these PCR products are immobilized on the surface. Subsequently, a measurement as described above is carried out.

Discussion

The inventors have shown that fluorescence melting curve analysis is a fast and cost-effective method that can be fully integrated with PCR for detection of aberrant DNA methylation patterns. Once the bisulfite conversion of sample DNA has been performed, screening of samples can be completed in less than 45 minutes by using standard PCR reagents. Also considering that the risk of PCR contamination is significantly reduced because no manual transfer of PCR products is required, this method provides an attractive alternative to traditional gel-based methylation assays.

Appropriate design of PCR primers is important for successful methylation resolution by melting curve analysis. First, the primers must discriminate between methylated and unmethylated alleles neither at the nucleotide level (18) nor at the amplification level (19). Second, because multiple melting domains in a PCR product result in a corresponding number of melting peaks (20), a change in the methylation status of a particular CpG dinucleotide will affect only the $T_m$ of the melting domain in which the CpG is located. Preferably, all CpG sites of the target region should be contained in one lower-melting domain of the amplified product. Modulation of melting profiles may easily be achieved by using one of several available computer algorithms in combination with PCR-based GC-clamping (21). The MELT94 algorithm used in this study produces theoretical $T_m$ values that are significantly lower than the experimental values, but is very accurate in predicting the domain structure of the DNA molecule (unpublished data).

Temperature transition rates and concentrations of salt and dye may have a significant impact on the width and absolute position of a PCR product's melting peak (20; 22; 23) and must be appropriately controlled for reproducible results. For routine high-throughput applications, the temperature transition rate might be chosen as the best compromise between speed and resolution. A too high transition rate may cause peak broadening that hampers differentiation between methylated and unmethylated alleles. As shown for the human SNRPN gene in FIG. 3, analysis of monoallelic methylation of a region containing 11 CpG sites at a transition rate of 0.1° C./s usually resulted in two overlapping but differentiable melting peaks with a $T_m$ difference of approximately 3° C. At this transition rate, the melting curve analysis could be completed within 4 minutes. Non-overlapping melting peaks may be obtained by lowering the temperature transition rate, increasing the number of CpG sites in the target sequence, or by increasing the accuracy of temperature control during melting analysis.

A potential pitfall inherent in melting curve analysis based on the use of SYBR Green I or other PCR-compatible double-stranded DNA-specific dyes is that it may not be possible to differentiate between the correct PCR product and unintended products, including primer dimers. Hence, PCR protocols must be developed that effectively prevent inadvertent amplification of unintended sequences, for example by the incorporation of 'hot-start' and 'touch-down' steps. Another potential source of unintended products is 'jumping PCR' (24) in which an extending primer jumps to another template during PCR. If the template DNA contains both methylated and unmethylated alleles, prematurely terminated products may extend templates of the opposite type due to the high sequence homology, which may lead to the in vitro formation of chimeric molecules with combined methylation patterns and intermediate $T_m$s.

Figure 4:
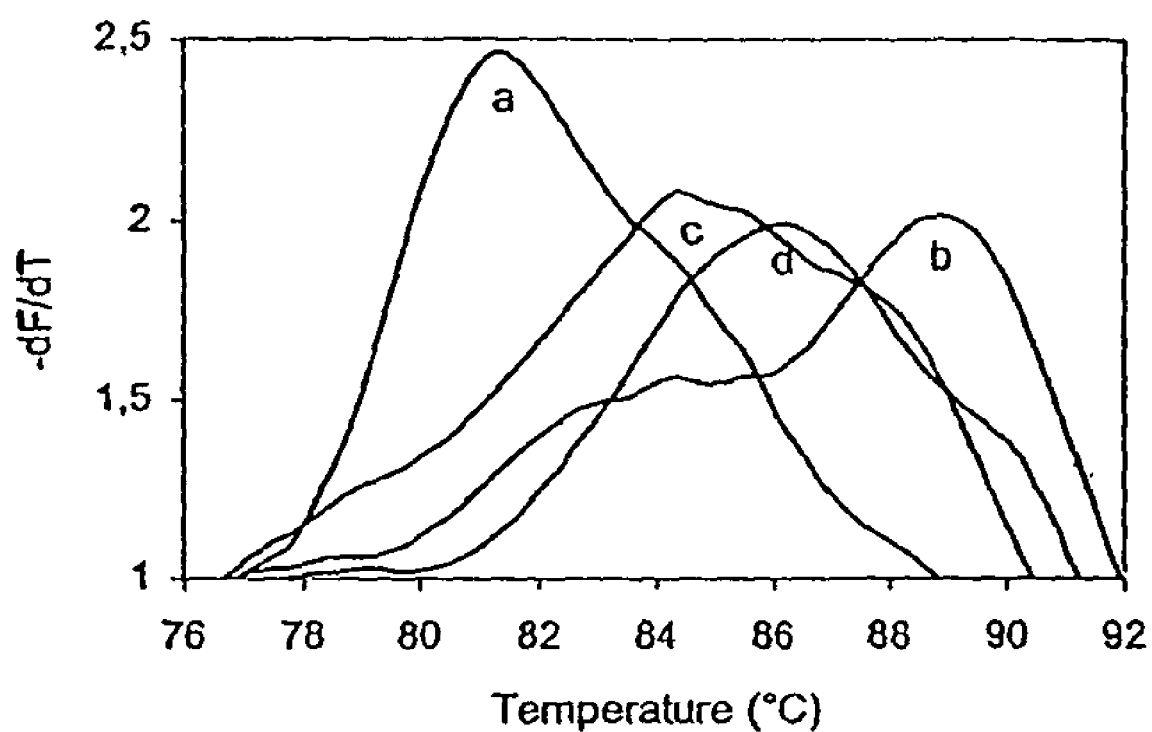
FIG. 4 shows fluorescence melting peaks for the $p15^{Ink4b}$ gene. Bisulfite-treated DNA was amplified from the two control cell lines, HL-60 (unmethylated, curve 'a') and MOLT-4 (fully methylated, curve 'b'), and from bone marrow cells from patients with AML (curves 'c' and 'd').

One of the strongest features of the present method is that it can resolve heterogeneous methylation patterns. Previous studies of bone marrow samples from patients with AML have demonstrated that the content and distribution of m$^5$C in the promoter sequences of some tumor suppressor genes may differ significantly between different cells from the same patient (11;17;25;26). Furthermore, heterogeneous methylation of promoter CpG islands in non-cancerous tissues has been demonstrated for the genes encoding prolactin and growth hormone (27), suggesting that this phenomenon may be more common in biological processes than previously appreciated. As shown for the p15$^{Ink4b}$ gene promoter in FIG. 4, heterogeneously methylated AML samples can be easily distinguished by melting analysis by showing a broader melting peak with an overall $T_m$ between the $T_m$s of the unmethylated and fully methylated alleles. Although melting curve analysis does not provide information on the methylation status of individual alleles or individual CpGs, it is highly useful for rapid screening of samples for overall methylation status at specific genes and loci.

Recently, a methylation method was developed that combines MSP with real-time quantitative PCR (28; 29). The major advantages of real-time MSP over conventional MSP are the in-tube format and its quantitative dimension. The drawbacks of this method are that it requires expensive hybridisation probes, standard curves must be generated in each setting, heterogeneous methylation may not be detected, and analysis of methylated and unmethylated alleles must be performed in separate tubes. Melting curve analysis, on the other hand, does not require any expensive reagents, resolves heterogeneous methylation, and detects methylated and unmethylated alleles in the same reaction in a semi-quantitative fashion.

REFERENCES

1. Jones, P. A. and Laird, P. W. (1999) *Nat. Genet.*, 21, 163-167.
2. Baylin, S. B., Herman, J. G., Graff, J. R., Vertino, P. M. and Issa, J. P. (1998) *Adv. Cancer Res.*, 72:141-96, 141-196.
3. Feinberg, A. P. (2000) *Curr. Top. Microbiol. Immunol.*, 249:87-99, 87-99.
4. Wang, R. Y., Gehrke, C. W. and Ehrlich, M. (1980) *Nucleic. Acids. Res.*, 8, 4777-4790.
5. Frommer, M., McDonald, L. E., Millar, D. S., Collis, C. M., Watt, F., Grigg, G. W., Molloy, P. L. and Paul, C. L. (1992) *Proc. Natl. Acad. Sci. USA*, 89, 1827-1831.
6. Herman, J. G., Graff, J. R., Myohanen, S., Nelkin, B. D. and Baylin, S. B. (1996) *Proc. Natl. Acad. Sci. U.S.A.*, 93, 9821-9826.
7. Gonzalgo, M. L. and Jones, P. A. (1997) *Nucleic. Acids. Res.*, 25, 2529-2531.
8. Sadri, R. and Hornsby, P. J. (1996) *Nucleic Acids Res.*, 24, 5058-5059.
9. Xiong, Z. and Laird, P. W. (1997) *Nucleic. Acids. Res.*, 25, 2532-2534.
10. Wittwer, C. T., Ririe, K. M., Andrew, R. V., David, D. A., Gundry, R. A. and Balis, U. J. (1997) *Biotechniques*, 22, 176-181.
11. Aggerholm, A., Guldberg, P., Hokland, M. and Hokland, P. (1999) *Cancer Res.*, 59, 436-441.
12. Zeschnigk, M., Lich, C., Buiting, K., Doerfler, W. and Horsthemke, B. (1997) *Eur. J. Hum. Genet.*, 5, 94-98.
13. Lerman L S, Silverstein K, Fripp B, Sauer P, Dresselhaus C. hhttp://web.mit.edu/osp/www/melt.html
14. Zeschnigk, M., Schmitz, B., Dittrich, B., Buiting, K., Horsthemke, B. and Doerfler, W. (1997) *Hum. Mol. Genet.*, 6, 387-395.
15. Guldberg, P., Grønbæk, K., Aggerholm, A., Platz, A., thor Straten, P., Ahrenkiel, V., Hokland, P. and Zeuthen, J. (1998) *Nucleic Acids Res.*, 26, 1548-1549.
16. Nicholls, R. D., Saitoh, S. and Horsthemke, B. (1998) *Trends Genet.*, 14, 194-200.
17. Dodge, J. E., List, A. F. and Futscher, B. W. (1998) *Int. J. Cancer*, 78, 561-567.
18. Clark, S. J., Harrison, J., Paul, C. L. and Frommer, M. (1994) *Nucleic. Acids. Res.*, 22, 2990-2997.
19. Warnecke, P. M., Stirzaker, C., Melki, J. R., Millar, D. S., Paul, C. L. and Clark, S. J. (1997) *Nucleic. Acids. Res.*, 25, 4422-4426.
20. Wartell, R. M. and Benight, A. S. (1985) *Phys. Rep.*, 126, 67-107.
21. Sheffield, V. C., Cox, D. R., Lerman, L. S. and Myers, R. M. (1989) *Proc. Natl. Acad. Sci. USA*, 86, 232-236.
22. Hillen, W., Goodman, T. C. and Wells, R. D. (1981) *Nucleic Acids Res.*, 9, 415-436.
23. Ririe, K. M., Rasmussen, R. P. and Wittwer, C. T. (1997) *Anal. Biochem.*, 245, 154-160.
24. Huang, L. M. and Jeang, K. T. (1994) *Biotechniques*, 16, 242-4, 246.
25. Cameron, E. E., Baylin, S. B. and Herman, J. G. (1999) *Blood*, 94, 2445-2451.
26. Melki, J. R., Vincent, P. C. and Clark, S. J. (1999) *Cancer Res.*, 59, 3730-3740.
27. Ngô, V., Gourdji, D. and Laverriere, J. N. (1996) *Mol. Cell Biol.*, 16, 3245-3254.
28. Eads, C. A., Danenberg, K. D., Kawakami, K., Saltz, L. B., Blake, C., Shibata, D., Danenberg, P. V. and Laird, P. W. (2000) *Nucleic Acids Res.*, 28, E32.
29. Lo, Y. M. D., Chan, L. Y., Chan, A. T., Leung, S. F., Lo, K. W., Zhang, J., Lee, J. C., Hjelm, N. M., Johnson, P. J. and Huang, D. P. (1999) *Cancer Res.*, 59, 5452-5455.

REFERENCES RELATING TO THE SECOND ASPECT OF THE INVENTION

Abrams, E. S. and Stanton, V. P. (1992). Use of denaturing gradient gel electrophoresis to study conformational transitions in nucleic acids. Methods Enzymol. 212, 71-104.

Ririe, K. M., Rasmussen, R. P., and Wittwer, C. T. (1997). Product differentiation by analysis of DNA melting curves during the polymerase chain reaction. Anal. Biochem. 245, 154-160.

Schaeffer, F., Kolb, A., and Buc, H. (1982). Point mutations change the thermal denaturation profile of a short DNA fragment containing the lactose control elements. Comparison between experiment and theory. EMBO J. 1, 99-105.

---

The invention claimed is:

1. A method of determining a methylation profile for a target nucleic acid sequence, said method comprising
   (a) treating the nucleic acid sequence with a bisulfite, to convert unmethylated cytosines within the nucleic acid sequence to uracil thereby creating a converted nucleic acid sequence; and
   (b) amplifying said converted nucleic acid sequence using oligonucleotide primers specific only for said converted nucleic acid sequence, wherein said primers do not discriminate between methylated and unmethylated alleles, said amplification conditions including the incorporation of a signal agent in the amplified nucleic acid, said signal agent being a double-stranded DNA dye capable of providing a distinction between double-stranded and single-stranded nucleic acid;
   and then, following steps (a) and (b),
   (c) detecting the amount of said signal agent during transition of the amplified nucleic acid between double-stranded and single-stranded as a result of a temperature change; and
   (d) determining the methylation profile of said target nucleic acid sequence by measuring the amount of signal agent detected during said temperature change,
wherein said determining step comprises resolving a heterogeneous methylation pattern, if present, in said target nucleic acid sequence.

2. A method according to claim 1 wherein the target nucleic acid sequence is from an animal.

3. A method according to claim 1, wherein the target nucleic acid sequence is from a human.

4. A method according to claim 1, wherein the target nucleic acid is from a tumour cell.

5. A method according to claim 1 wherein the target nucleic acid sequence is from a plant or a prokaryotic organism.

6. A method according to claim 1, wherein the bisulfite is sodium bisulfite.

7. A method of determining the existence of a nucleic acid methylation profile associated with a disease state, using a test nucleic acid from a candidate disease cell, said method comprising the steps of
   (a) treating the test nucleic acid sequence with a bisulfite, to convert unmethylated cytosines within the nucleic acid sequence to uracil, thereby creating a converted nucleic acid sequence; and
   (b) amplifying said converted nucleic acid sequence using oligonucleotide primers specific only for said converted nucleic acid sequence, wherein said primers do not discriminate between methylated and unmethylated alleles, said amplification conditions including the incorporation of a signal agent in the amplified nucleic acid, said signal agent being a double-stranded DNA dye capable of providing a distinction between double-stranded and single-stranded nucleic acid;
   and then, following steps (a) and (b),
   (c) detecting the amount of said signal agent during transition of the amplified nucleic acid between double-stranded and single-stranded as a result of a temperature change; and
   (d) determining the methylation profile of said test nucleic acid sequence by measuring the amount of signal agent detected during said temperature change and comparing the result with that obtained using control nucleic acid from a non-disease cell,
wherein said determining step comprises resolving a heterogeneous methylation pattern, if present, in said target nucleic acid sequence.

8. A method according to claim 7 wherein the disease state is selected from the group consisting of cancer, genetic disorders, metabolic diseases and age related disorders.

9. A method according to claim 8 wherein the disease state is cancer.

10. A method according to claim 7, wherein the bisulfite is sodium bisulfite.

11. A method according to claim 7, wherein the transition of the amplified nucleic acid is from double-stranded to single-stranded as a result of a temperature increase.

12. A method according to claim 11 wherein the test nucleic acid comprises a low-temperature control melting domain and a high-temperature melting domain (GC-clamp).

13. A method according to claim 12 wherein the low-temperature control melting domain and the high-temperature melting domain (GC-clamp) are incorporated into the test nucleic acid via the oligonucleotide primers.

* * * * *

SEQUENCE LISTING

<160> NUMBER OF SEQ ID NOS: 7

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 1
cgggcggggg catactcaaa ctaaaatata tactaaacct acc                    43

<210> SEQ ID NO 2
<211> LENGTH: 70
<212> TYPE: DNA
<213> ORGANISM: Artificial Sequence
<220> FEATURE:

-continued

<223> OTHER INFORMATION: Description of Artificial Sequence: Primer

<400> SEQUENCE: 2
cgcccgccgc gccccgcgcc cgtcccgccg ccccgcccg agagaagtta ttggtatagt    60
tgattttgtt                                                          70

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
cgcctgggag gggttttgtg ttttatt                                       27

<210> SEQ ID NO 4
<211> LENGTH: 66
<212> TYPE: DNA
<213> ORGANISM: Artificial Sequence
<220> FEATURE:
<223> OTHER INFORMATION: Description of Artificial Sequence: Primer

<400> SEQUENCE: 4
cgcccgccgc gccccgcgcc cgtcccgccg ccccgcccg ccattctatc tccaataaca    60
ccctaa                                                              66

<210> SEQ ID NO 5
<211> LENGTH: 166
<212> TYPE: DNA
<213> ORGANISM: Artificial Sequence
<220> FEATURE:
<223> OTHER INFORMATION: Description of Artificial Sequence: Final
      amplification product from HIC1 gene

<400> SEQUENCE: 5
cgcccgccgc gccccgcgcc cgtcccgccg ccccgcccg ataattagcg tattaagggt    60
tttttgtgcg acgtgattat cgtggtgtag aacgttttt ttcgcgcgta taagaacgtg   120
ttggcggtta gtagcgttta ttttaagttt ttggtgggcc gcccgc                 166

<210> SEQ ID NO 6
<211> LENGTH: 148
<212> TYPE: DNA
<213> ORGANISM: Artificial Sequence
<220> FEATURE:
<223> OTHER INFORMATION: Description of Artificial Sequence: Final
      amplification product from DAPK gene

<400> SEQUENCE: 6
cgcccgccgc gccccgcgcc cgtcccgccg ccccgcccg cgagttaacg tcggggattt    60 tgttttttt acgaggggga ttcggtaatt cgtagcggta gggtttgggg tcggcgtttg   120
ggagggattt gcgttttta tttccgcc                                     148

<210> SEQ ID NO 7
<211> LENGTH: 203
<212> TYPE: DNA
<213> ORGANISM: Artificial Sequence
<220> FEATURE:
<223> OTHER INFORMATION: Description of Artificial Sequence: Final
      amplification product from SNRPN gene

<400> SEQUENCE: 7
gcccgccccc gccgccctgc ccgcgccccg cgccgcccgc agagaagtta tcggtatagt    60

```
tgattttgtt cgttttatcg cgttattgat cgtttttag atagatgcgt taggtatttt        120
cggcggtcgt tttattttgc gttagattcg ttgtagtagc ggtaggtttc gtatatattt        180
tcgtttgagt atgcgccgcc cgc                                                203
```